United States Patent [19]

Trainor

[11] Patent Number: 4,873,221

[45] Date of Patent: Oct. 10, 1989

[54] DIFLUORO PEPTIDE COMPOUNDS

[75] Inventor: Diane A. Trainor, Glen Mills, Pa.

[73] Assignee: ICI Americas Inc., Wilmington, Del.

[21] Appl. No.: 51,952

[22] Filed: May 19, 1987

[30] Foreign Application Priority Data

Jun. 5, 1986 [GB] United Kingdom ............... 8613703

[51] Int. Cl.$^4$ ..................... A61K 37/43; C07K 5/08
[52] U.S. Cl. ..................................... 514/18; 514/19; 530/331
[58] Field of Search ................... 530/331; 514/18, 19

[56] References Cited

FOREIGN PATENT DOCUMENTS 0204571 10/1986 European Pat. Off. .
3604510 8/1986 Fed. Rep. of Germany .

OTHER PUBLICATIONS

Buehler et al., "Organic Syntheses", (1974), pp. 625 & 626.
Wagner et al., "Synthetic Organic Chemistry", (1953), pp. 303 & 324.
Jounral of Medicinal Chemistry 28, noll., (1985), 1553–1555.
J. Med. Chem., (1986), 2080–7, vol. 29.
Biochemistry, 24 (1985), 1813–1817.

*Primary Examiner*—Delbert R. Phillips
*Attorney, Agent, or Firm*—Rosemary M. Miano; Thomas E. Jackson

[57] ABSTRACT

The invention relates to selected difluoro compounds of formulae Ia, Ib and Ic (set out hereinafter) which are useful as inhibitors of human leukocyte elastase.

4 Claims, No Drawings

DIFLUORO PEPTIDE COMPOUNDS

This application is a continuation-in-part of U.S. Ser. No. 004,020, filed Jan. 16, 1987, and now abandoned.

BACKGROUND AND SUMMARY OF THE INVENTION

The present invention relates to certain difluoro peptide compounds which are human leukocyte elastase (HLE) inhibitors and are also useful as research tools in pharmacological and related studies and in the treatment of tissue degenerative diseases such as pulmonary emphysema, atherosclerosis, rheuma-toid arthritis and osteoarthritis in warm blooded animals. The invention also includes intermediates useful in the synthesis of these peptide derivatives, processes for preparing them, pharmaceutical compositions containing such peptide derivatives and methods for their use. Proline based peptide aldehydes are disclosed in European patent application No. 84302621.2. Fluoroketone inhibitors of hydrolytic enzymes are disclosed in Gelb, M.H. et al, *Biochemistry* (1985) 24, 1813-1817 for non-serine proteases. Imperiali, B. et al. *Tetra. Letters* (1986) 27, No. 2, 135-138 shows selected fluoromethyl ketones. Thaisrivongs, S. et al, *J. Med. Chem.* (1985) 28, No. 11, 1553-1555 discloses selected fluoro ketones as renin inhibitors.

DESCRIPTION OF THE INVENTION

The substituted peptides of the present invention may be represented by the following formulae Ia, Ib and Ic:
(Formula set out on pages following Examples) Ia
(Formula set out on pages following Examples) Ib
(Formula set out on pages following Examples) Ic
wherein
$R^1$ is alkyl;
$R^2$ is alkyl, substituted alkyl, aryl, substituted aryl, aralkyl or substituted aryl, aralkyl or substituted aralkyl;
$R^3$ is alkyl, substituted alkyl, cycloalkyl, substituted cycloalkyl, alkenyl, substituted alkenyl, aryl, substituted aryl, aralkyl, substituted aralkyl, an aliphatic heterocycle, a substituted aliphatic heterocycle, an aromatic heterocycle or a substituted aromatic heterocycle;
$R^4$ is hydrogen or methyl;
$R^B$ is selected from a group consisting of groups of fomula IIa and IIb:
(Formula set out on pages following Examples) IIa
(Formula set out on pages following Examples) IIb
wherein $R^6$ and $R^7$ are hydrogen, alkyl, substituted alkyl, aryl, substituted aryl, aralkyl, or substituted aralkyl;
$R^8$ is hydroxy, amino, (1-3C)alkoxy, (7-12C)aralkoxy, (6C) aryloxy, arylsulfonylamino wherein the aryl portion has 6 or 10 carbons, substituted arylsulfonylamino wherein the substituent is a member selected from the group consisting of fluoro, chloro, bromo and nitro, (1-15C)alkylsulfonylamino, phenylamino optionally substituted on the phenyl portion by a member selected for —COOH, —SO$_3$H, —PO$_3$H, tetrazolo, and (1-15-C)alkylsulfonylaminocarbonyl;
$R^C$ is selected from a group consisting of hydrogen and methyl; and
A is selected from a group consisting of

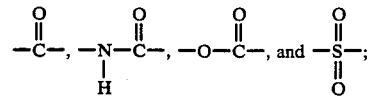

and salts therof, especially pharmaceutically acceptable salts.

More particular definitions for some of the groups defined above are as follows:
$R^1$ is an alkyl group containing from 1 to 5 carbons and more preferably from 2 to 5 carbons;
$R^2$ is selected from a group consisting of:
(I) an alkyl group containing from 1 to 10 carbons;
(II) an alkyl group containing from 1 to 6 carbons substituted by at least one member selected from a group consisting of:
(a) hydroxy;
(b) amino;
(c) alkylamino containing from 1 to 6 carbons;
(d) dialkylamino wherein each alkyl group contains from 1 to 6 carbons;
(e) alkanoyl containing from 2 to 6 carbons;
(f) arylcarbonyl wherein the aryl contains 6, 10 or 12 carbons;
(g) aralkanoyl containing 8 to 13 carbons;
(h) amido which may be attached to the alkyl group via either a nitrogen or carbon of said amido;
(i) alkylcarbonylamino wherein the alkyl group contains from 1 to 6 carbons;
(j) alkylaminocarbonyl wherein the alkyl group contains from 1 to 6 carbons;
(k) arylcarbonylamino wherein the aryl group contains 6, 10 or 12 carbons;
(l) aralkylcarbonylamino wherein the aralkyl group contains from 7 to 13 carbons;
(m) arylaminocarbonyl wherein the aryl group contains 6, 10 or 12 carbons;
(n) aralkylaminocarbonyl wherein the aralkyl group contains from 7 to 13 carbons;
(o) carboxy;
(p) aryloxycarbonyl wherein the aryl group contains 6, 10 or 12 carbons;
(q) aralkoxycarbonyl wherein the aralkoxy group contains from 7 to 13 carbons;
(r) alkanoyloxy containing from 2 to 6 carbons;
(s) aroyloxy wherein the aryl portion contains 6, 10 or 12 carbons;
(t) aralkanoyloxy containing from 8 to 14 carbons;
(u) alkylsulfonamido wherein the alkyl group contains from 1 to 6 carbons;
(v) aralkylsulfonamido wherein the aralkyl group contains from 7 13 carbons;
(w) arylsulfonamido wherein the aryl group contains 6, 10 or 12 carbons;
(x) acylsulfonamido (i.e. acylaminosulfonyl and sulfonylaminocarbonyl) (2 to 15 carbons) including acylsulfonamido wherein the acyl group contains 1 to 7 carbons when it is the terminal portion of the acylsulfonamide and provided that when the acylsulfonamido contains an aryl the aryl contains 6, 10 or 12 carbons and may be further substituted by a member selected from fluoro, chloro, bromo, iodo and nitro;

(y) alkoxycarbonyl wherein the alkoxy group contains from 1 to 6 carbons;
(z) aralkoxycarbonylamino containing from 8 to 13 carbons (e.g., benzyloxycarbonylamino);
  (aa) aryloxycarbonylamino wherein the aryloxy group contains 6, 10 or 12 carbons;
  (bb) alkoxycarbonylamino wherein the alkyloxy group contains from 1 to 6 carbons;
  (cc) aryl containing 6, 10 or 12 carbons (e.g., phenyl, biphenyl, napthyl);
  (dd) aryl containing 6, 10 or 12 carbons and substituted by 1 to 3 members selected from a group consisting of chloro, bromo, iodo, fluoro, trifluoromethyl, hydroxy, alkyl (1 to 6 carbons), alkoxy (1 to 6 carbons), alkanoyloxy (2 to 6 carbons), alkoxycarbonyl (1 to 6 carbons), carboxy, 5-tetrazolo, and acylsufonamido (i.e. acylaminosulfonyl and sulfonylaminocarbonyl) (2 to 15 carbons) and provided that when the acylsulfonamido contains an aryl the aryl contains 6, 10 or 12 carbons and may be further substituted by a member selected from fluoro, chloro, bromo, iodo and nitro;
  (ee) cycloalkyl containing from 3 to 15 carbons (e.g., cyclohexyl, adamantyl, norbornyl);
  (ff) alkylureido wherein the alkyl group contains from 1 to 6 carbons;
  (gg) aralkylureido containing from 8 to 13 carbons;
  (hh) arylureido wherein the aryl group contains 6, 10 or 12 carbons; and
  (III) an aryl group of 6 carbons, e.g. phenyl;
$R^3$ is selected from the group consisting of:
  (I) an alkyl group containing from 1 to 12 carbons;
  (II) an alkyl group containing from 1 to 12 carbons and from 1 to 4 hetero atoms each of which is selected independently from the group consisting of nitrogen and oxygen;
  (III) an alkyl group containing from 1 to 12 carbons and, optionally, 1 to 4 hetero atoms each of which is selected independently from the group consisting of nitrogen and oxygen, and substituted on at least one of carbon or nitrogen by 1 to 3 members selected independently from a group consisting of:
For carbon:
(a) hydroxy, provided that it may not be on a carbon directly bonded to A;
(b) amino, provided that it may not be on a carbon directly bonded to A;
(c) alkylamino containing from 1 to 6 carbons, provided that it may not be on a carbon directly bonded to A;
(d) dialkylamino wherein each alkyl group contains from 1 to 6 carbons, provided that it may not be on a carbon directly bonded to A;
(e) alkanoyl containing from 2 to 6 carbons;
(f) arylcarbonyl wherein the aryl contains 6, 10 or 12 carbons;
(g) aralkanoyl containing 8 to 13 carbons;
(h) amido which may be attached to the alkyl group via either a nitrogen or carbon of said amido;
(i) alkylcarbonylamino wherein the alkyl group contains from 1 to 6 carbons;
(j) alkylaminocarbonyl wherein the alkyl group contains from 1 to 6 carbons;
(k) arylcarbonylamino wherein the aryl group contains 6, 10 or 12 carbons;
(k)-(1) arylcarbonylamino wherein the aryl group contains 6, 10 or 12 carbons and is substituted by a member selected from carboxy, alkoxycarbonyl, where alkoxy is 1 to 3 carbons, 5-tetrazolo, and acylsulfonamido (i.e. acylaminosulfonyl and sulfonylaminocarbonyl) containing 2 to 15 carbons and provided that when the acylsulfonamido contains an aryl the aryl contains 6, 10 or 12 carbons and may be further substituted by a member selected from fluoro, chloro, bromo, iodo and nitro;
(l) aralkylcarbonylamino wherein the aralkyl group contains from 7 to 13 carbons;
(l)-(1) aralkylcarbonylamino wherein the aralkyl group contains 7 to 13 carbons and is substituted on the aryl portion by a member selected from carboxy, alkoxycarbonyl, where the alkoxy has 1 to 3 carbons, 5-tetrazolo, and acylsulfonamido (i.e. acylaminosulfonyl and sulfonylaminocarbonyl) containing 2 to 15 carbons and provided that when the acylsulfonamido contains an aryl the aryl contains 6, 10 or 12 carbons and may be further substituted by a member selected from fluoro, chloro, bromo, iodo and nitro;
(m) arylaminocarbonyl wherein the aryl group contains 6, 10 or 12 carbons;
(n) aralkylaminocarbonyl wherein the aralkyl group contains from 7 to 13 carbons;
(o) carboxy;
(p) aryloxycarbonyl wherein the aryl group contains 6, 10 or 12 carbons;
(q) aralkoxycarbonyl wherein the aralkoxy group contains from 7 to 13 carbons;
(r) alkanoyloxy containing from 2 to 6 carbons;
(s) aroyloxy wherein the aryl portion contains 6, 10 or 12 carbons;
(t) aralkanoyloxy containing from 8 to 13 carbons;
(u) alkylsulfonamido wherein the alkyl group contains from 1 to 6 carbons;
(u)-(1) cycloalkylsulfonamido wherein the cycloalkyl portion contains 3 to 15 carbons (e.g., cyclohexyl, adamantyl, norbornyl);
(v) aralkylsulfonamido wherein the aralkyl group contains from 7 to 13 carbons;
(w) arylsulfonamido wherein the aryl group contains 6, 10 or 12 carbons;
(x) acylsulfonamido (i.e. acylaminosulfonyl and sulfonylaminocarbonyl) (2 to 15 carbons) including acylsulfonamido wherein the acyl group contains 1 to 7 carbons when it is the terminal portion of the acylsulfonamide, and provided that when the acylsulfonamido contains an aryl the aryl contains 6, 10 or 12 carbons and may be further substituted by a member selected from fluoro, chloro, bromo, iodo and nitro;
(y) alkoxycarbonyl wherein the alkoxy group contains from 1 to 6 carbons;
(z) aralkoxycarbonylamino containing from 8 to 13 carbons (e.g., benzyloxycarbonylamino);
(z)-(1) aralkylaminocarbonyloxy containing 8 to 13 carbons;
(z)-(2) aryloxy wherein the aryl contains 6, 10 or 12 carbons;

(z)-(3) aryloxy wherein the aryl contains 6, 10 or 12 carbons and is substituted by a member selected from aminocarbonyl, aminocarbonylalkyl where the alkyl has 1 to 3 carbons, alkoxycarbonyl having 1 to 3 carbons, and carboxy;

(aa) aryloxycarbonylamino wherein the aryloxy group contains 6, 10 or 12 carbons;

(aa)-(1) arylaminocarbonyloxy wherein the aryl group contains 6, 10 or 12 carbons;

(bb) alkoxycarbonylamino wherein the alkyloxy group contains from 1 to 6 carbons;

(bb)-(1) alkoxycarbonylamino wherein the alkoxy group contains 1 to 6 carbons and is optionally bonded on carbon to a carbon of an aromatic heterocyclic group as described in (gg) under $R^3$;

(bb)-(2) alkoxycarbonylamino wherein the alkoxy group contains 1 to 6 carbons substituted by an aliphatic heterocyclic group as described in (ff) under $R^3$;

(bb)-(3) aryloxyalkylcarbonylamino wherein the aryl contains 6 or 10 carbons and the alkyl has 1 to 6 carbons;

(bb)-(4) alkylaminocarbonyloxy wherein the alkyl group contains 1 to 6 carbons;

(cc) aryl containing 6, 10 or 12 carbons (e.g., phenyl, naphthyl, biphenyl);

(cc)-(1) aryloxy containing 6, 10 or 12 carbons;

(dd) aryl containing 6, 10 or 12 carbons and substituted by 1 to 3 members independently selected from a group consisting of chloro, bromo, iodo, fluoro, hydroxy, trifluoromethyl, alkyl (1 to 6 carbons), alkoxy (1 to 6 carbons), alkanoyloxy (2 to 6 carbons), alkoxycarbonyl (2 to 6 carbons), carboxy, aminocarbonylalkyl (2 to 6 carbons), aminocarbonyl, 5-tetrazolo, and acylsulfonamido (i.e. acylaminosulfonyl and sulfonylaminocarbonyl) (2 to 15 carbons), and provided that when the acylsulfonamido contains an aryl the aryl contains 6, 10 or 12 carbons and may be further substituted by a member selected from fluoro, chloro, bromo, iodo and nitro;

(dd)-(1) aryloxy containing 6, 10 or 12 carbons and substituted on carbon by 1 to 3 members independently selected from a group consisting of chloro, bromo, iodo, fluoro, hydroxy, trifluoromethyl, alkyl (1 to 6 carbons), alkoxy (1 to 6 carbons), alkanoyloxy (2 to 6 carbons), alkoxycarbonyl (2 to 6 carbons), carboxy, aminocarbonylalkyl (2 to 6 carbons), aminocarbonyl, 5-tetrazolo, acylsulfonamido (i.e. acylaminosulfonyl and sulfonylaminocarbonyl) (2 to 15 carbons) and provided that when the acylsulfonylamido contains an aryl the aryl contains 6, 10 or 12 carbons and may be further substituted by a member selected from fluoro, chloro, bromo, iodo and nitro;

(ee) cycloalkyl containing from 3 to 15 carbons (e.g., cyclohexyl, adamantyl, norbornyl);

(ee)-(1) cycloalkyloxy containing from 3 to 15 carbons;

(ff) an aliphatic heterocyclic group of at least 4 atoms containing from 1 to 5 carbons and from 1 to 4 hetero atoms each of which is selected independently from a group consisting of nitrogen and oxygen (e.g., morpholine, piperazine), wherein the aliphatic heterocyclic group may optionally contain 1 or 2 double bond(s), which aliphatic heterocyclic group may be substituted at any nitrogen with an alkyl group containing from 1 to 6 carbons, an alkanoyl group containing from 1 to 6 carbons, an aryloxycarbonyl group wherein the aryl group contains 6, 10 or 12 carbons, an aralkyloxycarbonyl group wherein the aralkyl group contains from 7 to 13 carbons or an alkoxycarbonyl group wherein the alkyl group contains from 1 to 6 carbons;

(ff)-(1) an aliphatic heterocyclic oxy group wherein the oxy link is bonded directly to a carbon atom of the aliphatic heterocyclic group of at least 5 atoms containing from 1 to 5 carbons and from 1 to 4 hetero atoms each of which is selected independently from a group consisting of nitrogen and oxygen, (e.g., morpholine, piperazine), wherein the aliphatic heterocyclic group may optionally contain 1 or 2 double bond(s), which aliphatic heterocyclic group may be substituted at any nitrogen with an alkyl group containing from 1 to 6 carbons, an alkanoyl group containing from 1 to 6 carbons, an aryloxycarbonyl group wherein the aryl group contains 6, 10 or 12 carbons, an aralkyloxycarbonyl group wherein the aralkyl group contains from 7 to 13 carbons or an alkoxycarbonyl group wherein the alkyl group contains from 1 to 6 carbons;

(gg) an aromatic heterocyclic group containing (1) from 1 to 15 carbons and from 1 to 4 heteroatoms each of which is selected independently from a group consisting of sulfur, nitrogen and oxygen and (2) from 1 to 3 five or six-membered rings at least one of which is aromatic, and optionally, wherein up to 3 carbons of the aromatic ring(s) may be substituted with a member of a group consisting of fluoro, chloro, bromo, iodo, trifluoromethyl, alkyl containing from 1 to 6 carbons, alkoxy containing from 1 to 6 carbons, alkanoyl containing from 2 to 6 carbons, carboxy, aminocarbonylalkyl (2 to 6 carbons) and aminocarbonyl, and provided further that any nitrogen atom may be substituted by an alkyl group containing from 1 to 6 carbons;

(gg)-(1) an aromatic heterocyclic oxy group wherein the oxy link is bonded directly to a carbon of an aromatic heterocyclic group containing (1) from 1 to 15 carbons and from 1 to 4 heteroatoms each of which is selected independently from a group consisting of sulfur, nitrogen and oxygen and (2) from 1 to 3 five or six-membered rings at least one of which is aromatic, and optionally, wherein up to 3 carbons of the aromatic ring(s) may be substituted with a member of a group consisting of fluoro, chloro, bromo, iodo, trifluoromethyl, alkyl containing from 1 to 6 carbons, alkoxy containing from 1 to 6 carbons, alkanoyl containing from 2 to 6 carbons, carboxy, aminocarbonylalkyl (2 to 6 carbons) and aminocarbonyl, and provided further that any nitrogen atom may be substituted by an alkyl group containing from 1 to 6 carbons;

(hh) alkylureido wherein the alkyl group contains from 1 to 6 carbon atoms;

(hh)-(1) cycloalkylureido wherein the cycloalkyl group contains 3 to 15 carbons;

(ii) aralkylureido wherein the aralkyl group contains from 7 to 13 carbons;

(jj) arylureido wherein the aryl group contains 6, 10 or 12 carbons;

(jj)-(1) arylureido wherein the aryl group contains 6, 10 or 12 carbons and is substituted by 1 to 3 members selected independently from a group consisting of chloro, bromo, iodo, fluoro, hydroxy, trifluoromethyl, alkyl (1 to 6 carbons), alkoxy (1 to 6 carbons), alkanoyloxy (2 to 6 carbons), alkoxycarbonyl (2 to 6 carbons), carboxy, aminocarbonylalkyl (2 to 6 carbons), aminocarbonyl, 5-tetrazolo, and acylsulfonamido (i.e. acylaminosulfonyl and sulfonylaminocarbonyl) (2 to 15 carbons) including acylsulfonamido wherein the acyl group contains 1 to 7 carbons when it is the terminal portion of the acylsulfonamide and provided that when the acylsulfonamido contains an aryl the aryl contains 6, 10 or 12 carbons and may be further substituted by a member selected from fluoro, chloro, bromo, iodo and nitro;

For nitrogen (a) alkyl of 1 to 3 carbons;

(b) alkanoyl containing from 2 to 6 carbons;

(c) arylcarbonyl wherein the aryl contains 6, 10 or 12 carbons;

(d) aralkanoyl containing 8 to 14 carbons;

(e) formyl;

(f) an aliphatic heterocyclic group as defined in (ff) for the carbon substituents wherein the nitrogen is bonded directly to a carbon of the aliphatic heterocyclic group;

(g) an aromatic heterocyclic group as defined in (gg) for the carbon substituents wherein the nitrogen is bonded directly to a carbon of the aromatic heterocyclic group;

(IV) an aryl group containing 6, 10 or 12 carbons;

(V) an aryl group containing 6, 10 or 12 carbons suitably substituted by 1 to 3 members selected independently from a group consisting of fluoro, chloro, bromo, iodo, trifluoromethyl, hydroxy, alkyl containing from 1 to 6 carbons, alkanoyloxy (2 to 6 carbons), alkoxy containing from 1 to 6 carbons, alkoxycarbonyl containing from 2 to 6 carbons, carboxy, alkylcarbonylamino wherein the alkyl group contains 1 to 6 carbons, 5-tetrazolo, and acylsulfonamido (i.e. acylaminosulfonyl and sulfonylaminocarbonyl) containing from 2 to 15 carbons, and provided that when the acylsulfonamido contains an aryl the aryl contains 6, 10 or 12 carbons and may be further substituted by a member selected from fluoro, chloro, bromo, iodo and nitro;

(VI) a cycloalkyl group containing from 3 15 carbons (e.g., cyclohexyl, adamantyl, norbornyl);

(VI)-(1) a cycloalkyl group containing from 3 to 15 carbons (e.g., cyclohexyl, adamantyl, norbornyl), substituted by a member selected from the group consisting of carboxy, alkoxycarbonyl wherein the alkoxy group contains 1 to 4 carbons, 5-tetrazolo, and acylsulfonamido (i.e. acylaminosulfonyl and sulfonylaminocarbonyl) (2 to 15 carbons) including acylsulfonamido wherein the acyl group contains 1 to 7 carbons when it is the terminal portion of the acylsulfonamide and provided that when the acylsulfonamido contains an aryl the aryl contains 6, 10 or 12 carbons and may be further substituted by a member selected from fluoro, chloro, bromo, iodo and nitro;

(VII) an aliphatic heterocyclic group of at least 5 atoms containing from 1 to 5 carbons and from 1 to 4 hetero atoms each of which is selected independently from a group consisting of nitrogen and oxygen, (e.g., morpholine, piperazine) which may be substituted at any nitrogen with a member selected from a group consisting of an alkyl group containing from 1 to 6 carbons, an alkanoyl group containing from 1 to 6 carbons, an aryloxycarbonyl group wherein the aryl group contains 6, 10 or 12 carbons, an aralkoxycarbonyl group wherein the aralkyl group contains from 7 to 13 carbons and an alkoxycarbonyl group containing from 2 to 7 carbons, provided that when A is OCO or NHCO then A must be bonded to a carbon atom of the aliphatic heterocyclic group;

(VIII) an aromatic heterocyclic group containing (a) from 1 to 15 carbons and from 1 to 4 heteroatoms each of which is selected independently from the group consisting of sulfur, nitrogen and oxygen, and (b) from 1 to 3 five or six-membered rings at least one of which is aromatic, and optionally, wherein up to 3 carbons of the aromatic ring(s) may be substituted at any carbon with a member of a group consisting of fluoro, chloro, bromo, iodo, trifluoromethyl, alkyl containing from 1 to 6 carbons, alkoxy containing from 1 to 6 carbons, alkanoyl containing from 2 to 6 carbons, carboxy, and provided furhter that any nitrogen may be substituted by an alkyl group containing from 1 to 6 carbons, provided that when A is OCO or NHCO then A must be bonded to a carbon of the aromatic heterocycle;

(IX) an alkenyl group of 2 to 10 carbons, having at least one double bond; and (X) an alkenyl group of 2 to 10 carbons, having at least one double bond and substituted by a member selected from a group consisting of (a) aryl of 6 or 10 carbons;

(b) aryl of 6 or 10 carbons substituted by 1 to 3 members selected independently from a group consisting of chloro, bromo, iodo, fluoro, hydroxy, trifluoromethyl, alkyl (1 to 6 carbons), alkoxy (1 to 6 carbons), alkanoyloxy (2 to 6 carbons), alkoxycarbonyl (2 to 6 carbons) carboxy, 5-tetrazolo, and acylsulfonamido (i.e. acylaminosulfonyl and sulfonylaminocarbonyl) (2 to 15 carbons) and provided that when the acylsulfonamido contains an aryl the aryl contains 6, 10 or 12 carbons and may be further substituted by a member selected from fluoro, chloro, bromo, iodo and nitro; and (c) ureidocarbonyl;

$R^4$ is selected from a group consisting of hydrogen and methyl;

$R^6$ and $R^7$ are each independently selected from hydrogen and the group defined for $R^2$;

$R^C$ is selected to be hydrogen.

More particular values for compounds of the invention include those formed with the following members of the groups defined above:

$R^1$ is an alkyl group containing 3 carbons, especially isopropyl;

$R^2$ is selected from a group consisting of:

(I) an alkyl group containing from 1 to 4 carbons;

(II) an alkyl group containing from 1 to 4 carbons substituted by at least one member selected from a group consisting of:

(e) alkanoyl containing from 2 to 3 carbons;

(f) arylcarbonyl wherein the aryl contains 6 or 10 carbons (e.g., phenyl or naphthyl);

(g) aralkanoyl containing 8 carbons (e.g., phenylacetyl);

(h) amido which may be attached to the alkyl group via either a nitrogen or carbon of said amido;
(i) alkylcarbonylamino wherein the alkyl group contains from 1 to 2 carbons;
(j) alkylaminocarbonyl wherein the alkyl group contains from 1 to 2 carbons;
(k) arylcarbonylamino wherein the aryl group contains 6 carbons (e.g., phenyl);
(l) aralkylcarbonylamino wherein the aralkyl group contains 7 carbons;
(m) arylaminocarbonyl wherein the aryl group contains 6 carbons (e.g. phenyl);
(n) aralkylaminocarbonyl wherein the aralkyl group contains 7 carbons;
(o) carboxy;
(p) aryloxycarbonyl wherein the aryl group contains 6 carbons (e.g. phenyl);
(q) aralkoxycarbonyl wherein the aralkoxy group contains 7 carbons;
(r) alkanoyloxy containing from 1 to 2 carbons;
(s) aroyloxy wherein the aryl portion contains 6 carbons (e.g. phenyl);
(t) aralkanoyloxy containing 8 carbons;
(u) alkylsulfonamido wherein the alkyl group contains from 1 to 6 carbons;
(v) aralkylsulfonamido wherein the aralkyl group contains from 7 to 13 carbons (e.g., 1-naphthylmethylsulfonylamino or 4-phenylbutylsulfonylamino);
(w) arylsulfonamido wherein the aryl group contains 6 or 10 carbons;
(x) acylsulfonamido containing 2 to 15 carbons (e.g., phenylsulfonylaminocarbonyl);
(y) alkoxycarbonyl wherein the alkoxy group contains 1 or 2 carbons;
(z) aralkoxycarbonylamino wherein the aralkoxy group contains 7 carbons (e.g., benzyloxycarbonylamino);
(aa) aryloxycarbonylamino wherein the aryloxy group contains 6 carbons;
(bb) alkoxycarbonylamino wherein the alkyloxy group contains from 1 to 3 carbons;
(cc) aryl containing 6 or 10 carbons (e.g., phenyl or naphthyl);
(dd) aryl containing 6 or 10 carbons and substituted by 1 to 3 members selected from a group consisting of chloro, bromo, iodo, fluoro, trifluoromethyl, hydroxy, alkyl (1 to 2 carbons), alkoxy (1 to 2 carbons), alkanoyloxy (2 to 6 carbons), alkoxycarbonyl (2 to 3 carbons), carboxy, 5-tetrazolo, and acylsulfonamido (2 to 15 carbons);
(ee) cycloalkyl containing from 3 to 15 carbons (e.g., cyclohexyl, adamantyl, norbornyl);
(ff) alkylureido wherein the alkyl group contains from 1 to 2 carbons;
(gg) aralkylureido wherein the aralkyl group contains 7 carbons;
(hh) arylureido wherein the aryl group contains 6 or 10 carbons; and
(III) an aryl group of 6 carbons (e.g. phenyl);
$R^3$ is selected from a group consisting of:
(I) an alkyl group containing from 1 to 12 carbons;
(II) an alkyl group containing from 1 to 12 carbons and from 1 to 4 heteroatoms each of which is selected independently from a group consisting of nitrogen and oxygen;
(III) an alkyl group containing from 1 to 12 carbons and, optionally, 1 to 4 heteroatoms each of which is selected independently from a group consisting of nitrogen and oxygen, and substituted on at least one of carbon or nitrogen by 1 to 3 members selected independently from a group consisting of:

For carbon:
(e) alkanoyl containing from 2 to 6 carbons;
(f) arylcarbonyl wherein the aryl contains 6, 10 or 12 carbons;
(g) aralkanoyl containing 8 to 13 carbons;
(h) amido which may be attached to the alkyl group via either a nitrogen or carbon of said amido;
(i) alkylcarbonylamino wherein the alkyl group contains from 1 to 6 carbons;
(j) alkylaminocarbonyl wherein the alkyl group contains from 1 to 6 carbons;
(k) arylcarbonylamino wherein the aryl group contains 6 or 10 carbons;
(k)-(1) arylcarbonylamino wherein the aryl group contains 6 or 10 carbons and is substituted by a member selected from carboxy, alkoxycarbonyl, where alkoxy is 1 to 3 carbons, 5-tetrazolo, and acylsulfonamido containing 2 to 15 carbons;
(l) aralkylcarbonylamino wherein the aralkyl group contains from 7 to 13 carbons;
(l)-(1) aralkylcarbonylamino wherein the aralkyl group contains 7 to 13 carbons and is substituted by a member selected from carboxy, alkoxycarbonyl, where the alkoxy has 1 to 3 carbons, 5-tetrazolo, and acylsulfonamido containing 2 to 15 carbons;
(m) arylaminocarbonyl wherein the aryl group contains 6 or 10 carbons;
(n) aralkylaminocarbonyl wherein the aralkyl group contains from 7 to 13 carbons;
(o) carboxy;
(p) aryloxycarbonyl wherein the aryl group contains 6 or 10 carbons;
(q) aralkoxycarbonyl wherein the aralkoxy group contains from 7 to 13 carbons;
(r) alkanoyloxy containing from 2 to 3 carbons;
(s) aroyloxy wherein the aryl portion contains 6 or 10 carbons;
(t) aralkanoyloxy containing from 8 to 13 carbons;
(u) alkylsulfonamido wherein the alkyl group contains from 1 to 6 carbons;
(u)-(1) cycloalkylsulfonamido wherein the cycloalkyl portion contains 3 to 15 carbons (e.g., the cycloalkyl may be cyclohexyl, adamantyl, norbornyl), e.g., 1-adamantylsulfonylamido;
(v) aralkylsulfonamido wherein the aralkyl group contains from 7 to 13 carbons;
(w) arylsulfonamido wherein the aryl group contains 6 or 10 carbons;
(x) acylsulfonamido containing 2 to 15 carbons;
(y) alkoxycarbonyl wherein the alkoxy group contains from 1 to 3 carbons;
(z) aralkoxycarbonylamino containing from 8 to 13 carbons (e.g., benzyloxycarbonylamino);
(z)-(1) aralkylaminocarbonyloxy wherein the aralkyl group contains 7 to 12 carbons;
(z)-(2) aryloxy wherein the aryl contains 6, 10 or 12 carbons;
(z)-(3) aryloxy wherein the aryl contains 6, 10 or 12 carbons and is substituted by a member selected from aminocarbonyl, aminocarbonylalkyl where the alkyl has 1 to 3 carbons, alkoxycarbonyl having 2 to 4 carbons, and carboxy;

(aa) aryloxycarbonylamino wherein the aryloxy group contains 6 or 10 carbons;

(aa)-(1) arylaminocarbonyloxy wherein the aryl group contains 6 or 10 carbons (e.g. phenyl or naphthyl);

(bb) alkoxycarbonylamino wherein the alkyloxy group contains from 1 to 6 carbons;

(bb)-(1) alkoxycarbonylamino wherein the alkoxy group contains 1 to 6 carbons and is optionally bonded on a carbon of an aromatic heterocyclic group as described in (gg) under $R^3$;

(bb)-(2) alkoxycarbonylamino wherein the alkoxy group contains 1 to 6 carbons substituted by an aliphatic heterocyclic group as described in (ff) under $R^3$;

(bb)-(3) aryloxyalkylcarbonylamino wherein the aryl contains 6 or 10 carbons (e.g. phenyl or naphthyl) and the alkyl has 1 to 6 carbons;

(bb)-(4) alkylaminocarbonyloxy wherein the alkyl group contains 1 to 6 carbons;

(cc) aryl containing 6 or 10 carbons (e.g., phenyl or naphthyl);

(cc)-(1) aryloxy containing 6 or 10 carbons;

(dd) aryl containing 6, 10 or 12 carbons and substituted by 1 to 3 members independently selected from the group consisting of chloro, bromo, iodo, fluoro, hydroxy, trifluoromethyl, alkyl (1 to 6 carbons), alkoxy (1 to 6 carbons), alkanoyloxy (2 to 6 carbons), alkoxycarbonyl (2 to 6 carbons), carboxy, aminocarbonylalkyl (2 to 6 carbons), aminocarbonyl, 5-tetrazolo, and acylsulfonamido (2 to 15 carbons);

(dd)-(1) aryloxy containing 6, 10 or 12 carbons and substituted by 1 to 3 members independently selected from a group consisting of chloro, bromo, iodo, fluoro, hydroxy, trifluoromethyl, alkyl (1 to 6 carbons), alkoxy (1 to 6 carbons), alkanoyloxy (2 to 6 carbons), alkoxycarbonyl (2 to 6 carbons), carboxy, acylsulfonamido (2 to 15 carbons) aminocarbonylalkyl (2 to 6 carbons), aminocarbonyl and 5-tetrazolo;

(ee) cycloalkyl containing from 3 to 15 carbons (e.g., cyclohexyl, adamantyl or norbornyl);

(ee)-(1) cycloalkyloxy containing from 3 to 15 carbons;

(ff) an aliphatic heterocyclic group of at least 5 atoms containing from 1 to 5 carbons and from 1 to 4 heteroatoms each of which is selected independently from a group consisting of nitrogen and oxygen (e.g., morpholine, piperazine), wherein the aliphatic heterocyclic group may optionally contain 1 or 2 double bond(s), which aliphatic heterocyclic group may be substituted at any nitrogen with an alkyl group containing from 1 to 6 carbons, an alkanoyl group containing from 2 to 6 carbons, an aryloxycarbonyl group wherein the aryl group contains 6, 10 or 12 carbon atoms, an aralkyloxycarbonyl group wherein the aralkyl group contains from 7 to 13 carbons or an alkoxycarbonyl group wherein the alkyl group contains from 1 to 6 carbons (e.g., morpholinyl, piperazinyl);

(ff)-(1) an aliphatic heterocyclic oxy group wherein the oxy link is bonded directly to a carbon atom of an aliphatic heterocyclic group of at least 5 atoms containing from 1 to 5 carbons and from 1 to 4 heteroatoms each of which is selected independently from a group consisting of nitrogen and oxygen, wherein the aliphatic heterocyclic group may optionally contain 1 or 2 double bonds(s), which aliphatic heterocyclic group may be substituted at any nitrogen with an alkyl group containing from 1 to 6 carbons, an alkanoyl group containing from 2 to 6 carbons, an aryloxycarbonyl group wherein the aryl group contains 6, 10 or 12 carbons, an aralkyloxycarbonyl group wherein the aralkyl group contains from 7 to 13 carbons or an alkoxycarbonyl group wherein the alkyl group contains from 1 to 6 carbons;

(gg) an aromatic heterocyclic group containing (1) from 1 to 15 carbons and from 1 to 4 heteroatoms each of which is selected independently from the group consisting of sulfur, nitrogen and oxygen and (2) from 1 to 2 five or six-membered rings at least one of which is aromatic, and optionally, wherein up to 3 carbons of the aromatic ring(s) may be substituted with a member of a group consisting of fluoro, chloro, bromo, iodo, trifluoromethyl, methyl, alkoxy containing from 1 to 2 carbons, alkanoyl containing from 2 to 3 carbons, carboxy, aminocarbonylalkyl (2 to 6 carbons) and aminocarbonyl, and provided further that any nitrogen atom may be substituted by an alkyl group containing from 1 to 6 carbon atoms;

(gg)-(1) an aromatic heterocyclic oxy group wherein the oxy link is bonded directly to a carbon of an aromatic heterocyclic group containing (1) from 1 to 15 carbons and from 1 to 4 heteroatoms each of which is selected independently from a group consisting of sulfur, nitrogen and oxygen and (2) from 1 to 2 five or six-membered rings at least one of which is aromatic, and optionally, wherein up to 3 carbons of the aromatic ring(s) may be substituted with a member of a group consisting of fluoro, chloro, bromo, iodo, trifluoromethyl, methyl, alkoxy containing from 1 to 2 carbons, alkanoyl containing from 2 to 3 carbons, carboxy, aminocarbonylalkyl (2 to 6 carbons) and aminocarbonyl, and provided further that any nitrogen atom may be substituted by an alkyl group containing from 1 to 6 carbons;

(hh) alkylureido wherein the alkyl group contains from 1 to 6 carbons;

(hh)-(1) cycloalkylureido wherein the cycloalkyl group contains from 3 to 15 carbons;

(ii) aralkylureido wherein the aralkyl group contains from 7 to 13 carbons;

(jj) arylureido wherein the aryl group contains 6 or 10 carbons;

(jj)-(1) arylureido wherein the aryl group contains 6 or 10 carbons and is substituted by 1 to 3 members selected from a group consisting of chloro, bromo, iodo, fluoro, hydroxy, trifluoromethyl, alkyl (1 to 6 carbons), alkoxy (1 to 6 carbons), alkanoyloxy (2 to 6 carbons), alkoxycarbonyl (2 to 6 carbons), carboxy, acylsulfonamide (2 to 15 carbons), aminocarbonylalkyl (2 to 6 carbons), aminocarbonyl and 5-tetrazolo;

For nitrogen:
(a) alkyl of 1 to 3 carbons;
(b) alkanoyl containing from 2 to 6 carbons;
(c) arylcarbonyl wherein the aryl contains 6, 10 or 12 carbons;
(d) aralkanoyl containing 8 to 14 carbons;
(e) formyl;
(f) an aliphatic heterocyclic group as defined in (ff) for the carbon substituents wherein the nitrogen is bonded directly to a carbon of the aliphatic heterocyclic group;
(g) an aromatic heterocyclic amino group as defined in (gg) for the carbon substituents wherein the nitrogen is bonded directly to a carbon of the aromatic heterocyclic group;

(IV) an aryl group containing 6 or 10 carbons;

(V) an aryl group containing 6 or 10 carbons suitably substituted by 1 to 3 members selected independently from a group consisting of fluoro, chloro, bromo, iodo, trifluoromethyl, alkyl containing from 1 to 6 carbons, alkoxy containing from 1 to 6 carbons, alkanoyloxy (2 to 6 carbons), alkoxycarbonyl containing from 2 to 6 carbons, carboxy, alkylcarbonylamino wherein the alkyl group contains 1 to 6 carbons, 5-tetrazolo, and acylsulfonamido containing from 2 to 15 carbons (e.g., 4-[(4-chlorophenyl)sulfonylaminocarbonyl]phenyl or 4-[(4-bromophenyl)sulfonylaminocarbonyl]phenyl);

(VI) a cycloalkyl group containing from 3 to 15 carbons (e.g., cyclohexyl, adamantyl, norbornyl);

(VI)-(1) a cycloalkyl group containing from 3 to 15 carbons (e.g., cyclohexyl, adamantyl or norbornyl), substituted by a member selected from a group consisting of carboxy, alkoxycarbonyl wherein the alkoxy group contains 1 to 4 carbons, 5-tetrazolo, and acylsulfonamido containing from 2 to 15 carbons;

(VII) an aliphatic heterocyclic group of at least 5 atoms containing from 1 to 5 carbons and from 1 to 4 hetero atoms each of which is selected independently from a group consisting of nitrogen and oxygen, (e.g., morpholinyl, piperazinyl), which may be substituted at any nitrogen with a member selected from a group consisting of methyl, an alkanoyl group containing from 2 to 6 carbon atoms, an aryloxycarbonyl group wherein the aryl group contains 6 or 10 carbons, an aralkoxycarbonyl group wherein the aralkyl group contains 7 carbons and an alkoxycarbonyl group containing from 2 to 3 carbons, provided that when A is OCO or NHCO, then A must be bonded to a carbon of the aliphatic heterocyclic group;

(VIII) an aromatic heterocyclic group containing (a) from 1 to 15 carbons and from 1 to 4 heteroatoms each of which is selected independently from a group consisting of sulfur, nitrogen and oxygen, and (b) from 1 to 2 five or six-membered rings at least one of which is aromatic, and optionally, wherein up to 3 carbons of the aromatic ring(s) may be substituted at any carbon atom with a member of a group consisting of fluoro, chloro, bromo, iodo, trifluoromethyl, methyl, alkoxy containing from 1 to 2 carbons, alkanoyl containing from 2 to 3 carbons, carboxy, and provided further that any nitrogen may be substituted by an alkyl group containing from 1 to 6 carbons, provided that when A is OCO or NHCO then A must be bonded to a carbon of the aromatic heterocycle;

(IX) an alkenyl group of 2 to 10 carbons, having at least one double bond;

(X) an alkenyl group of 2 to 10 carbons, having at least one double bond and substituted by a member selected from a group consisting of
(a) aryl of 6 or 10 carbons;
(b) aryl of 6 or 10 carbons substituted by 1 to 3 members selected independently from a group consisting of chloro, bromo, iodo, fluoro, hydroxy, trifluoromethyl, alkyl (1 to 6 carbons), alkoxy (1 to 6 carbons), alkanoyloxy (2 to 6 carbons), alkoxycarbonyl (2 to 6 carbons), carboxy, acylaminosulfonyl (2 to 15 carbons) and 5-tetrazolo; and
(c) ureidocarbonyl; and $R^4$ is hydrogen;

Even more particular values for $R^B$ include —CH(CH$_2$O)COOCH$_3$, —CH(CH$_2$O)CONH$_2$, —CH(CH$_2$OH)CONHCH(CH$_2$O)—(CONH$_2$), —CH(CH$_2$O)COOCH$_3$, —CH(CH$_2$O)COOH, CH$_2$COOCH$_3$, CH$_2$COOH, CH(CH$_2$O)CONHCH$_2$COOCH$_3$, CH(CH$_2$O)CONHCH$_2$COOH, CH[(CH$_2$)$_4$NHOCOCH$_2$O]COOCH$_2$O, CH[(CH$_2$)$_4$NHOCOCH$_2$O]COOH, CH[(CH$_2$)$_2$OCOCH$_2$O]COOCH$_2$O, CH(CH$_2$O)COOCH$_2$O, and CH$_2$COOCH$_2$O.

Still more particular values for the groups defined above when compounds of formula Ib are selected are as follows: $R^1$:isopropyl; $R^3$:benzyl; A:OCO; $R^C$:H.

In compounds of formula Ib, when $R^B$ is formula IIa, particular values for $R^6$, $R^7$ and $R^8$ are: $R^6$:CH$_2$OH, OCH$_2$; $R^7$:H, OCH$_2$; $R^8$:NH$_2$, OCH$_3$, OH.

In compounds of formula Ib, when $R^B$ is formula IIb, particular values for $R^6$ and $R^8$ are: $R^6$:CH$_2$O, CH$_2$OH, H; $R^8$:NH$_2$, OCH$_3$, OH, OCH$_2$O.

The title compounds of Examples 11, 13 and 14 are especially preferred.

The salts of the compounds of formulae Ia, Ib and Ic include pharmaceutically acceptable base or acid addition salts such as those made with a mineral acid, e.g., hydrochloric, or an organic acid such as citric, maleic, fumaric or acetic. Base-addition salts include those made with alkali metal hydroxides such as sodium hydroxide, alkali metal carbonates and bicarbonates, alkaline earth hydroxides and organic amine salts. Such salts may be prepared by dissolving the peptide derivative in a mixture of water and a water-miscible organic solvent, adding an aqueous solution of the base and recovering the salt from the aqueous solution.

The preferred compounds of the present invention are of the S configuration (i.e., that of the naturally occurring L-amino acids) at chiral centers identified by * in formulae IIIa, IIIb and IIIc below (or identified by * in formulae IIId and IIIe for specific values of $R^B$) and the methods of synthesis described below provide isomers with the S configuration at the chiral center identified by symbol # or isomeric mixtures as a result of the R and S configurations at the chiral center identified by the symbol #. It is generally preferred that the compounds have the S configuration at the center identified by the symbol #. (Note that Formulae IIId and IIIe correspond to groups IIa and IIb).

(Formula set out on pages following Examples) IIIa
(Formula set out on pages following Examples) IIIb
(Formula set out on pages following Examples) IIIc
(Formula set out on pages following Examples) IIId
(Formula set out on pages following Examples) IIIe As will be appreciated by those skilled in the art, the activity of the individual isomers is not the same, and it is therefore preferred to utilize the more active isomer.

The present invention includes compounds resulting from the S and/or R configuration at the chiral center labelled #.

$R^A$, $R^B$, $R^1$, $R^2$ and $R^3$ may have chiral centers. The present invention includes compounds of formula Ia, Ib and Ic wherein the chiral centers included in $R^A$, $R^B$, $R^1$, $R^2$ and $R^3$ are of the S and/or R configurations.

As will be appreciated by those skilled in the art, the difluoro ketone derivatives can exist as solvates, particularly hydrates, formulae IVa, IVb and IVc, and these are encompassed by the present invention.

(Formula set out on pages following Examples) IVa
(Formula set out on pages following Examples) IVb
(Formula set out on pages following Examples) IVc It is preferred to prepare the difluoro peptides of the present invention from commercially available alpha amino acids (i.e., those in which the $NH_2$ group is attached to the carbon atom next to the —COOH group). Because of this, the preferred $R^2$, $R^6$ and $R^7$ moieties in the above formulae for tripeptide derivatives are those obtained from one of the following amino acids: alanine, valine, norvaline, leucine, isoleucine, norleucine, phenylalanine, triptophan, tyrosine, asparagine, glutamine, aspartic acid, glutamic acid, lysine, threonine, serine, alphaaminobutyric acid, and phenylglycine.

According to a further feature of the invention there are provided pharmaceutical compositions comprising a pharmaceutically effective amount of at least one peptide derivative of formula Ia, Ib or Ic and a pharmaceutically acceptable diluent or carrier.

The difluoro peptide compounds of formulae Ia, Ib and Ic may be prepared as follows.

Method A

A compound of formula Ia, Ib or Ic may be prepared from the corresponding alcohol of formula VIIIa, VIIIb or VIIIc:

(Formula set out on pages following Examples) VIIIa
(Formula set out on pages following Examples) VIIIb
(Formula set out on pages following Examples) VIIIc by an oxidative process. Methods which are useful include the use of oxalyl chloride, DMSO and a tertiary amine (see Marx, M., et al., *J. Org. Chem.*, (1984) 49, 788–793, with the best results being obtained with 10–20 equivalents of oxidizing agent), the use of acetic anhydride and DMSO, the use of chromium trioxide pyridine complex in methylene chloride, and the use of Dess-Martin periodinane [1,1,1-triacetoxy-2,1-benzoxiodol-3(3H)-one] (method of Dess, D. B. et al., *J. Org. Chem.*, (1983) 48, 4155–56).

An alcohol of formula VIIIa, VIIIb or VIIIc may be prepared from the corresponding aldehyde of formula VIa, VIb or VIc:

(Formula set out on pages following Examples) VIa
(Formula set out on pages following Examples) VIb
(Formula set out on pages following Examples) VIc by reacting the aldehyde with ethyl 2-bromo-2,2-difluoroacetate (obtained from SCM, Specialty Chemicals) and Zn in refluxing THF (see Hallinan, E. A., et al., *Tetrahedron Letters*, (1984) 25 (#22), 2301–2302) to give a compound of the following formula VIIa, VIIb or VIIc, respectively, (Formula set out on pages following Examples) VIIa
(Formula set out on pages following Examples) VIIb
(Formula set out on pages following Examples) VIIc which in turn may be reacted with an amine of formula V:

(Formula set out on pages following Examples) V and tetramethylguanidine and $CHCl_3$ at 0° C. to room temperature to afford the particular compound of formula VIIIa, VIIIb or VIIIc. (See R. H. Abeles, et al., *Biochemistry*, (1985) 24, 1813).

A compound of formula VIIIa, VIIIb or VIIIc may be converted into a new compound of formula VIIIa, VIIIb or VIIIc with a different value for $R^3$-A- via the formation of a corresponding compound of formula XIa, XIb or XIc:

(Formula set out on pages following Examples) XIa
(Formula set out on pages following Examples) XIb
(Formula set out on pages following Examples) XIc followed by reaction with the appropriate activated carbonyl or sulfonyl compound. For example, compounds of formulas VIIIa, VIIIb and VIIIc when $R^3$-A is benzyloxycarbonyl, may be converted by catalytic hydrogenolysis into the amino amides of formula XIa, XIb and XIc, respectively, which in turn can be reacted with a selected activated carbonyl or sulfonyl compound (e.g., isocyanate, acid chloride, chloroformate or sulfonyl chloride) or reacted with an acid of formula $R^3COOH$ using standard peptide coupling procedures as described above to give the new compounds of formula VIIIa, VIIIb and VIIIc, respectively.

An aldehyde of formula VIa, (Formula set out one pages following Examples) VIa
VIb or VIc may be prepared by oxidation of the corresponding alcohol of formula XIVa, XIVb or XIVc:

(Formula set out on pages following Examples) XIVa
(Formula set out on pages following Examples) XIVb
(Formula set out on pages following Examples) XIVc (e.g., oxidation conditions as described in M. Marx, et al., *J. Org. Chem.*, (1984) 49, 788–793), or by hydrolysis or transacetalization of the corresponding acetal of formula XVa, XVb or XVc:

(Formula set out on pages following Examples) XVa
(Formula set out on pages following Examples) XVb
(Formula set out on pages following Examples) XVc See, for example, the preparation of such compounds as described in European Patent Application No. 84302621.2.

A compound of formula XIVb or XIVc (for use in making compounds of formula VIb or VIc, respectively) may be prepared by reacting an amino alcohol of formula XVI:

(Formula set out on pages following Examples) XVI with an appropriate free acid of formula XVIIb or XVIIc:

(Formula set out on pages following Examples) XVIIb
(Formula set out on pages following Examples) XVIIc by standard peptide coupling procedures using methods commonly known to those skilled in the art, such as those described in M. Bodanszky, *Principles of Peptide Synthesis*, Springer-Verlag, Berlin, (1984), and *The Peptides. Analysis, Synthesis* and *Biology* (ed. E. Gross and J. Meinhofer), Vols. 1–5, (Academic Press, New York) 1979–1983. A compound of formula XVIIb or XVIIc may be prepared by standard peptide coupling and deprotection procedures as described above. The amino alcohols of formula XVI (when not commercially available) may be prepared from the corresponding alpha-amino acids of the formula $H_2NCHR^1COOH$ by reaction with a reducing agent such as diborane. See U.S. Pat. No. 3,935,280 to Lane. A compound of formula XIVa may be prepared by reacting a compound of formula XVI with the appropriate activated carbonyl or sulfonyl compound (for example, isocyanate, carbonate, acid chloride, chloroformate or sulfonyl chloride) or with an acid of formula $R^3COOH$ using standard peptide coupling procedures as described above.

Similarly, a compound of formula XVb or XVc may be prepared by reacting an amino acetal of formula XVIIIa: (Formula set out on pages following Examples) XVIIIa with an appropriate acid of formula XVIIb or XVIIc by standard peptide coupling procedures; and a compound of formula XVa may be prepared by reacting a compound of formula XVIIIa with the appropriate activated carbonyl or sulfonyl compound. The amino acetal of formula XVIIIa can be prepared as described in Examples (1a–1d).

An acetal of formula XVa, XVb or XVc may be prepared, when appropriate, by an acid catalyzed acetalization of a compound of formula VIa, VIb or VIc (e.g., with triethylorthoformate in absolute ethanol acidified with p-toluenesulfonic acid at room temperature) and converted to a new compound of formula XVa, XVb or XVc with a different value for $R^3$-A- via the formation of a corresponding compound of formula XVIIIa, XVIIIb or XVIIIc:

(Formula set out on pages following Examples) XVIIIa (Formula set out on pages following Examples) XVIIIb (Formula set out on pages following Examples) XVIIIc followed by reaction with the appropriate activated carbonyl or sulfonyl compound. For example, compounds of formula XVa, XVb and XVc when $R^3$-A is benzyloxycarbonyl, may be converted by catalytic hydrogenolysis into the amino acetals of formula XVIIIa, XVIIIb and XVIIIc, respectively, which in turn can be reacted with a selected activated carbonyl or sulfonyl compound (e.g., isocyanate, acid chloride, chloroformate or sulfonyl chloride) or reacted with an acid of formula $R^3COOH$ using standard peptide coupling procedures as described above to give the new compounds of formula XVa, XVb and XVc, respectively.

An alternate method for the preparation of a compound of formula VIIIb or VIIIc from a compound of formula VIIb or VIIc respectively, comprises reacting a compound of formula VIIb or VIIc with about 1.25 equivalents of 1N NaOH in $CH_3OH$ to give a corresponding compound of formula IXb or IXc, respectively, (Formula set out on pages following Examples) IXb (Formula set out on pages following Examples) IXc followed by reacting a compound of formula IXb or IXc with a compound of formula V:

(Formula set out on pages following Examples) V using HOBT, WSCDI and THF.

Amines of formula V are generally commercially available or may be prepared by standard techniques of organic chemistry, including standard peptide coupling and protection procedures as referenced above, and by analogy with the synthesis of known, structurally similar compounds.

Method B

A compound of formula Ia, Ib or Ic may be prepared from the corresponding acid of formula XXVIIa, XXVIIb or XXVIIc:

(Formula set out on pages following Examples) XXVIIa (Formula set out on pages following Examples) XXVIIb (Formula set out on pages following Examples) XXVIIc by coupling the acid with an amine of formula V (using similar conditions to those described above for the conversion of IXc to VIIIc) to afford the corresponding compound of formula Ia, Ib or Ic. A starting acid of formula XXVIIa, XXVIIb or XXVIIc may be obtained, for example, by hydrolyzing the corresponding ester such as the ethyl ester of formula XXVIa, XXVIb or XXVIc:

(Formula set out on pages following Examples) XXVIa (Formula set out on pages following Examples) XXVIb (Formula set out on pages following Examples) XXVIc using a similar method to that described above for the hydrolysis of a compound of formula VIIc to a compound of formula IXc. A starting ester of formula XXVIa, XXVIb or XXVIc may be obtained, for example, by oxidation of the corresponding alcohol of formula VIIa, VIIb or VIIc using one of the oxidation methods described in Method A.

(Formula set out on pages following Examples) VIIa
(Formula set out on pages following Examples) VIIb
(Formula set out on pages following Examples) VIIc

Method C

A compound of formula Ia, Ib or Ic where $R^2$, $R^3$, or $R^B$, contains a carboxy group may be prepared by decomposing the ester group of a corresponding compound of formula Ia, Ib or Ic where $R^2$, $R^3$ or $R^B$ contains an ester group. The ester groups contained by $R^2$, $R^3$ and $R^B$ of compounds of formula Ia, Ib and Ic described above include aryloxycarbonyl wherein the aryl group contains 6, 10 or 12 carbons, aralkoxycarbonyl wherein the aralkoxy group contains from 7 to 13 carbons, and alkoxycarbonyl wherein the particular alkoxy group contains from 1 to 3, 1–4, 1–5 or 1–6 carbons, as well as those resulting when $R^8$ is (1–3C)alkoxy, (7–12-C)aralkoxy and (6C)aryloxy.

It will be appreciated that the decomposition can be performed using any one of a variety of procedures well known in the art of organic chemistry. Thus, it may be carried out, for example, by conventional hydrolysis under acid or base conditions, adjusted as necessary to minimize any hydrolytic removal of other functional groups in the molecule. Also, when the ester is an aralkoxycarbonyl group, such as benzyloxycarbonyl, it may be possible to carry out the decomposition by reductive means, for example, by the use of hydrogen at about atmospheric pressure in the presence of a suitable catalyst, such as palladium or platinum, conveniently on charcoal as a support.

A preferred method for decomposing an ester of formula Ia, Ib or Ic comprises reacting the ester with a suitable base, for example, an alkali or alkaline earth metal hydroxide or carbonate (such as lithium hydroxide, potassium hydroxide, sodium hydroxide, calcium hydroxide or potassium carbonate) in a suitable, aqueous solvent or diluent, for example, water, optionally together with a water-miscible organic cosolvent, such as methanol, and conveniently at or near ambient temperature. When such a method is employed, the resultant carboxylic acid of formula Ia, Ib or Ic where $R^2$, $R^3$ or $R^B$ contains a carboxy group is initially obtained as the corresponding salt of the base used for the hydrolysis and may be isolated as such or converted to the free acid form by a conventional acidification procedure.

Method D

A compound of formula Ia, Ib or Ic where $R^2$, $R^3$ or $R^B$ contains an acylsulfonamide group of the sulfonamidocarbonyl type (including when $R^8$ is arylsulfonamido) may be prepared by reacting the corresponding compound of formula Ia, Ib or Ic where $R^2$, $R^3$ or $R^B$ contains a carboxy group or when $R^8$ is hydroxy, with an appropriate sulfonamide in the presence of a dehydrating agent, for example, with 1-ethyl-3-(3-dimethylaminopropyl)carbodiimide, or with a hydrochloride or hydrobromide salt thereof optionally together with an organic base, for example, 4-(dimethylamino)-pyridine, in the presence of a suitable solvent or diluent, for example, dichloromethane, at a temperature in the range of, for example, 10° to 50° C., but preferably at or near ambient temperature.

As will be apparent to one skilled in the art, it may be desired to convert a compound of formula Ia, Ib or Ic into another compound of formula Ia, Ib or Ic using a standard method well known in the art, such as, for example, conversion of an acid or ester into the corresponding amide.

Also, it may be desired to optionally use a protecting group during all or portions of the above described processes; the protecting group may then be removed when the final compound is to be formed. (See Greene, T. W., *Protective Groups in Organic Synthesis,* Wiley-Interscience, New York (1981).)

When a pharmaceutically acceptable salt is desired or required, it may be obtained using standard procedures well known in the art, for example, by further reacting a suitably acidic compound of formula Ia, Ib or Ic with a suitable base affording a physiologically acceptable cation or by further reacting a sufficiently basic compound of formula Ia, Ib or Ic with a suitable acid affording a physiologically acceptable anion.

Inhibition Measurements

The ability of compounds of the invention to act as elastase inhibitors may be initially determined by the ability of a compound of the invention to inhibit the action of human leukocyte elastase (HLE) on a low molecular weight peptide substrate. The potency of an inhibitor is evaluated by obtaining a kinetic determination of the dissociation constant, $K_i$, of the complex formed from the interaction of the inhibitor with HLE. The substrate used was the anilide methoxysuccinyl-L-alanyl-L-alanyl-L-prolyl-L-valine-p-nitroanilide as described by K. Nakajima et al. in *J. Biol. Chem.*, (1979) 254, 4027–4032 and by T. Teshima et al. in *J. Biol. Chem.*, (1982) 257, 9, 5085–5091. The HLE enzyme used in these studies may be obtained from Elastin Products of St. Louis, Mo. or can be purified according to B. R. Viscarello et al. in *Preparative Biochemistry,* (1983) 13, 57–67 as follows, all work being done in a cold room at 4° C.

Salt Extraction-DNase Treatment: The starting material, 193 g of purulent sputum, was homogenized with 200 ml of cold distilled water and centrifuged at 30,000×gravity for 20 min. at 4° C. The supernatant was discarded and the pellet extracted with high salt and treated with DNase as per the method of D. Y. Twumasi et al. in *J. Biol. Chem.*, (1977) 252, 1917–1926. Chromatography on Elastin Agarose: The precipitate from the DNase digest was taken up in two 40 ml portions of 50 mM Tris, 1.0M NaCl, pH 8; the suspension was centrifuged and the resulting supernatant applied directly to a column of soluble elastin-Sepharose 4B (2.5×20 cm). The column was washed with equilibrating buffer (50 mM Tris, 50 mM NaCl, pH 8.0) until the optical density at 280 nm ($OD_{280}$) of the eluate returned to baseline. Additional contaminating protein was eluted with two column volumes of 50 mM acetate, 1.0M NaCl, pH 5.0. Elastase and cathepsin G (HLC-G) were finally eluted with 50 mM acetate, 1.0M NaCl, 20% DMSO, pH 5.0. The column was developed at 6 ml/min with the collection of 10 ml fractions. The active fractions were pooled, dialyzed vs. two 6 liter changes of 50 mM acetate, 0.1M NaCl, pH 5.5, and concentrated to 40 ml on an Amicon ® ultrafiltration unit (YM-10 membrane). CM-Chromatography: The concentrated active fraction was applied to a column of CM-Sephadex ® C-50 (2.2×10 cm) previously equilibrated with 50 mM acetate, 0.1M NaCl, pH 5.5 and the column then washed with this buffer to remove contaminating protein. Elution was continued with 50 mM acetate, 0.2M NaCl, pH 5.5 and resulted in the displacement of a peak of activity assayed against Bz-L-Phe-L-Val-L-Arg-pNA. HLE was next eluted with the acetate buffer containing 0.45M NaCl, while elution of HLC-G required the presence of 1.0M NaCl in the buffer as described by R. Martodam et al. in *Preparative Biochemistry,* (1979) 9, 15–31. This column was developed at 30 ml/hr with the collection of 5.5 ml fractions. From the thus purified HLE, a standard rate of production of p-nitroaniline was measured at 25° C. spectrophotometrically in the visible spectrum at 410 nanometers with automatic data acquisition from a Cary 210 spectrophotometer obtained from Varian Associates. Reactions were initiated by injection of 10 microliters of the HLE solution into a 3 milliliter cuvette containing 2.89 milliliters of buffer (10 millimolar sodium phosphate, 500 millimolar NaCl, pH 7.6), 50 microliters substrate solution in DMSO, and 50 microliters of DMSO. Initial, steady-state reaction velocities of p-nitroaniline production were calculated by a fit of the experimental data to a linear dependence on time by linear least squares. This velocity, determined with no inhibitor present, was used as a standard in the calculation of inhibitor $K_i$ values.

As a general rule, the peptide derivatives of the present invention were found to be "slow-binding" inhibitors of HLE and therefore required special methods of analysis to accurately determine $K_i$ values for their inhibition of HLE (see Williams, J. W. and Morrison, J. F., *Meth. Enz.* (1979) 63, 437 for a description of these methods.) In a typical experiment, 2.89 ml of buffer (10 millimolar sodium phosphate, 500 millimolar sodium chloride, pH 7.6), 50 microliters of inhibitor solution in DMSO, and 50 microliters of substrate solution in DMSO were added to a 3 milliliter cuvette. The cuvette was stoppered, inverted several times to mix its contents and maintained at (25° C.) in the spectrophotometer. After a period of five minutes to allow the reaction solution to come to thermal equilibrium, 10 microliters of stock enzyme solution were added to the cuvette to initiate the reaction. Duplicate or triplicate runs were done at zero inhibitor concentration and at least three non-zero inhibitor concentrations. $K_i$ values were calculated according to methods outlined in the above reference by Williams and Morrison. The $K_i$ values for selected compounds were less than $10^{-7}$.

Animal Models

Animal models of emphysema include intratracheal (i.t.) administration of an elastolytic protease to cause a slowly progressive, destructive lesion of the lung. These lesions are normally evaluated a few weeks to a few months after the initial insult. However, these proteases also induce a lesion that is evident in the first few hours. The early lesion is first hemorrhagic, progresses to an inflammatory lesion by the end of the first 24 hours and resolves in the first week post insult. To take advantage of this early lesion, the following model was used.

Hamsters are first lightly anesthetized with methohexital sodium (Brevital ® from Eli Lilly). Phosphate buffered saline (PBS) pH 7.4, either alone or containing 400 µg of human leukocyte elastase (HLE), is then administered directly into the trachea. Twenty-four hours later the animals are killed and the lungs removed and carefully trimmed of extraneous tissue. Following determination of wet lung weight, the lungs are lavaged with PBS and total lavaegable red and white cells recovered are determined. The values for wet lung weights, total lavageable red cells and total lavageable whife cells are elevated in a dose-dependent manner following administration of HLE. Compounds that are effective elastase inhibitors can prevent or diminish the severity of the enzyme-induced lesion resulting in lower wet lung weight and reduced values for total lavageable cells, both red and white, relative to administration of HLE alone. Compounds can be evaluated by administering them either with or at various times prior to administration of HLE to determine their utility in preventing an HLE lesion. Compounds of this invention produced statistically significant reductions in wet lung weight and total lavageable cells relative to HLE alone.

Compounds of the present invention exhibited activity in at least one of the tests described above under Inhibition Measurement or Animal Model. It should be noted that there was not always a direct correlation between the activities of the compounds measured as $K_i$ values in the Inhibition Measurement test and the reduced values for total lavageable cells and wet lung weights relative to the administration of HLE alone obtained in the Animal Model test. It is thought that the Animal Model test is more predictive of the activity of such compounds in the treatment of emphysema.

Pharmacokinetics: Male Syrian hamsters (80 to 120 g) are injected intravenously with the test compound. Prior to injection and at varying time periods thereafter, they are lightly anesthetized with ether and blood samples of approximately 0.2 ml each are withdrawn by cardiac puncture. The blood is expressed into 2 ml centrifuge tubes and allowed to clot for one hour. The sample is then centrifuged and the serum removed.

Drug levels are determined by first inactivating endogenous elastase inhibitors by incubation of 50 microliters of serum with an equal volume of buffer containing 5 mg/ml bovine pancreatic trypsin for 5 min. The trypsin inactivated serum (10 microliters) is then added to a 0.52 ml cuvette containing buffer made 20 nM with respect to HLE. After an additional 30 min. incubation, the reaction is started by the addition of substrate (350 microliters) (MeOSuc-L-Ala-L-Ala-L-Pro-L-Val-pNA, 1.6 mM) and the reaction monitored spectrophotometrically at a wavelength of 410 nM. For comparative purposes, serum persistence of the test compounds is determined in the following manner:

Percent inhibition of serum samples was calculated as follows:

$$\text{percent inhibition} = \frac{V_o - V_i}{V_o} \times 100$$

The compounds of the present invention may be administered to a warm-blooded animal in need thereof, particularly a human, for the treatment of conditions of pulmonary emphysema, atherosclerosis, rheumatoid arthritis, and osteo arthritis, but in particular for emphysema. The mode of administration may be oral, parenteral, including the subcutaneous deposit by means of an osmotic pump, or via a powdered or liquid aerosol. These may be conventionally formulated in an oral or parenteral dosage form by compounding about 10 to 250 mg per unit of dosage with conventional vehicle, excipient, binder, preservative, stabilizer, flavor or the like as called for by accepted pharmaceutical practice e.g. as described in U.S. Pat. No. 3,755,340. For parenteral administration, a 1 to 10 ml intravenous, intramusular or subcutaneous injection would be given containing about 0.02 to 10 mg/kg of body weight of a compound of the invention 3 or 4 times daily. The injection would contain a compound of the invention in an aqueous isotonic sterile solution or suspension optionally with a preservative such as phenol or a solubilizing agent such as ethylenediaminetetraacetic acid (EDTA). In a powdered aerosol, compounds of the invention may be administered in the same manner as cromolyn sodium via a Spinhaler ® turbo-inhaler device obtained from Fisons Corp. of Bedford, Mass. at a rate of about 0.1 to 50 mg per capsule, 1 to 8 capsules being administered daily for an average human. Each capsule to be used in the Spinhaler ® contains the required amount of a compound of the invention with the remainder of the 20 mg capsule being a pharmaceutically-acceptable carrier such as lactose. In a liquid aerosol, the compounds of the invention are administered at the rate of about 100 to 1000 micrograms per "puff" or activated release of a standard volume of propellant. The liquid aerosol would be given at the rate of 1 to 8 puffs per day with variation in dosages due to the severity of the condition being treated, the weight of the patient and the particle size distribution of the aerosol since smaller particles will achieve greater lung penetration. Propellants, e.g., a fluorinated hydrocarbon or isobutane, containers, valves and actuators for liquid aerosols are described by L. Lachman et al. in "The Theory and Practice of Industrial Pharmacy", Lea and Febiger, Philadelphia (1976).

In the following Examples and throughout the specification, the following abbreviations are used: atm (atmospheres) with $1.013 \times 10^5$ Pascals=1 atm; bp (boiling point); °C. (degrees Centigrade); g (grams); hr (hours); mg (milligrams); min (minutes); ml (milliliters); mmol (millimoles); mp (melting point); N (normal); nm (nanometers); nM (nanomolar); $R_f$(relative mobility in TLC); TLC (thin layer chromatography); DCC (dicyclohexylcarbodiimide); DMF (dimethylformamide); DMSO (dimethyl sulfoxide); Et$_2$O (diethyl ether); EtOAc (ethyl acetate); HOAc (acetic acid); WSCDI (water soluble carbodiimide; 1-ethyl-3-(3-dimethylaminopropyl)carbodiimide hydrochloride); Bz (benzoyl); HOBT (1-hydroxybenzotriazole); MeOH (methyl alcohol); Pd/C (palladium on charcoal catalyst); pNA (paranitroanilide); DMPA (4-dimethylaminopyridine); φ (phenyl group); NMM (N-methylmorpholine); THF (tetrahydrofuran); CBZ (benzyloxycarbonyl); t-BOC (tertiarybutyloxycarbonyl); $t_R$ (HPLC retention time in min); HPLC (high performance liquid chromatography); TEA (triethylamine); TFA (trifluoroacetic acid); $Ac_2O$ (acetic anhydride); RT (room temperature); e.g. (for example); supra (above); DAST (diethylaminosulfurtrifluoride); vs. (versus); Dibal (diisobutylaluminum hydride); and Zorbax® ODS analytical column (4.6 mm×25 cm) also called "$C_{18}$ column"; Phenomenex Zorbax $C_8$25 cm×4.6 mm, also called "$C_8$ column". In addition, C, H, N, etc. (the conventional symbols for the elements) are used, and conventional abbreviations for amino acids, e.g. proline (Pro), valine (Val) etc. are also used. It is to be understood that generic terms such as "(1-10C)alkyl" include both straight and branched chain alkyl radicals, but references to individual alkyl radicals such as "propyl" include only the straight chain ("normal") radical, branched chain isomers such as "isopropyl" being specifically referred to. $^1H$ NMR data is given for values of delta using tetramethylsilane as an internal standard. Where needed, multiple runs of selected processes were done to obtain additional product.

Flash chromatography was carried out on Merck Kieselgel (Art 9385) and column chromatography on Merck Kieselgel 60 (Art 7734) [these materials were obtained from E. Merck, Darmstadt, W. Germany] or flash and column chromatographies were done on an acidic silica gel (J. T. Baker Chemical Co., low pH, Number 7290-R); thin layer chromatography (TLC) was carried out on Analtech 0.25 mm silica gel GHLF plates (Art 21521), obtainable from Analtech, Newark, DE, USA;

None of the compounds tested have been observed to be toxic.

EXAMPLE 1

N-[2,2-Difluoro-5-methyl-1,3-dioxo-4-[[(phenylmethoxy)carbonyl]amino]hexyl]-L-phenylalanine methyl ester (Formula Ia, $R^1$=CH(CH$_3$)$_2$, $R^3A$=φCH$_2$OCO—, $R^B$=Formula IIb, $R^6$=CH$_2$φ, $R^8$=OCH$_3$, $R^C$=H)

a. N-Benzyloxycarbonyl-L-valinol (Formula XIVa, $R^3A$=φCH$_2$OCO—, $R^1$=CH(CH$_3$)$_2$)

Benzyl chloroformate (91.0 g, 0.532 mol, 95% purity) was added dropwise over a period of 1 hr to a pre-cooled (0° C.) solution of L-valinol (50.0 g, 0.484 mol) and triethylamine (60.0 g, 0.6 mol) in CHCl$_3$ (1500 ml). The reaction mixture was stirred for 1 hr. at 0° C. and then allowed to warm to room temperature over 2 hr. The reaction mixture was concentrated under vacuum. EtOAc (1500 ml) was added to the resulting residue and the organic solution was washed with aqueous 1N NaOH and brine. The organic phase was dried over MgSO$_4$, filtered and concentrated under vacuum. The resulting residue was purified by flash chromatography on a column of silica gel (6 cm×30 cm) using a stepwise gradient of Et$_2$O:hexane (1:5) followed by pure Et$_2$O to give the product (91.4 g) as a white waxy solid; TLC, $R_f$=0.23, silica gel, hexane:Et$_2$O (50:50).

b. N-Benzyloxycarbonyl-L-valinal (Formula VIa, $R^3A$=φCH$_2$OCO—, $R^1$=CH(CH$_3$)$_2$)

A solution of DMSO (107.2 g, 1.372 mol) in CH$_2$Cl$_2$ (150 ml) was added dropwise over 0.5 hr to a pre-cooled (−60° C.), stirred solution of oxalyl chloride (87.1 g, 0.686 mol) in CH$_2$Cl$_2$ (800 ml) under a nitrogen atmosphere. The temperature of the mixture rose to −45° C. The reaction mixture was then warmed to −30° C. A solution of the product of Example 1a (81.5 g, 0.343 mol) in CH$_2$Cl$_2$ (300 ml) was added dropwise over 45 min at −30° C. The reaction mixture was stirred for 50 min at −25° C., cooled to −40° C. and a solution of diisopropylethyl amine (177.4 g, 1.372 mol) in CH$_2$Cl$_2$ (250 ml) was added dropwise over 45 min at −40° C. The reaction mixture was stirred for 1 hr as it warmed to room temperature. The reaction mixture was diluted with CH$_2$Cl$_2$ (1500 ml) and the organic phase was washed with aqueous 1N HCl and then concentrated under vacuum to give the product (98 g) as a green oil which was used immediately without further purification; TLC, $R_f$=0.48, silical gel, hexane:Et$_2$O (50:50).

c. N-Benzyloxycarbonyl-L-valinal diethylacetal (Formula XVa, $R^3A$=φCH$_2$OCO—, $R^1$=CH(CH$_3$)$_2$)

Triethyl orthoformate (700 g, 4.723 mol), absolute EtOH (800 ml) and p-toluenesulfonic acid monohydrate (5.0 g, 0.026 mol) were added to the product of Example 1b (81 g, 0.343 mol). The mixture was stirred for 10 min at room temperature and then concentrated under vacuum. The resulting residue was dissolved in Et$_2$O and washed with saturated aqueous NaHCO$_3$. The organic phase was dried over Na$_2$SO$_4$, filtered and concentrated under vacuum to give a crude product. This product was purified by flash chromatography with silica gel using a stepwise gradient of hexane through mixtures of CH$_2$Cl$_2$:hexane to EtOAc:CH$_2$Cl$_2$ (30:70) to give the product as a pale yellow oil; TLC, $R_f$=0.21, silica gel, CH$_2$Cl$_2$:petroleum ether (50:50).

d. L-Valinal diethylacetal (Formula XVIIIa, $R^1$=CH(CH$_3$)$_2$)

A mixture of a product made by the method of Example 1c (147.8 g, 0.478 mol) and 10% Pd/C (10 g) in EtOAc (1500 ml) was stirred under H$_2$ (1 atm) until 2500 ml of H$_2$ was consumed. Twice during this time the reaction was interrupted and 10% Pd/C (10 g) was added. The reaction mixture was then filtered through a pad oof diatomaceous earth. 10% Pd/C (10 g) was added and the reaction mixture stirred until 10.92 liters of H$_2$ was consumed. The reaction mixture was filtered through diatomaceous earth and the filtrate was concentrated under vacuum to give the product (78.8 g) as a pale yellow oil; [alpha]$_D^{25}$=+7.8.

e. (Formula VIIa, $R^3A$=0CH$_2$OCO-, $R^1$=CH(CH$_3$)$_2$)

The compound of Example 1b (3.0 g, 12.7 mmol), ethyl 2-bromo-2,2-difluoroacetate (2.58 g, 12.7 mmol) and Zn dust (1.22 g) were refluxed in THF (30 ml) for 0.5 hr. under N$_2$. Additional Zn dust (1.22 g) and ethyl 2-bromo-2,2-difluoroacetate (2.58 g, 12.7 mmol) were added and the resulting solution refluxed for an additional hour. The solution was cooled to room temperature and ethyl acetate (150 ml) was added. The ethyl acetate solution was washed with 1M KHSO$_4$ and brine, dried (Na$_2$SO$_4$), filtered and the solvent removed under reduced pressure to give a crude product (2.4 g). The product was purified by flash chromatography on silica gel with an eluent of ethyl acetate/hexane (35:65) to give the final product (0.9 g) as an oil; TLC, $R_f$=0.55, ethyl acetate:hexane (35:65).

f. (Formula VIIIa, $R^1$=CH(CH$_3$)$_2$, $R^3A$=0CH$_2$OCO-, $R^B$=Formula IIb, $R^6$=CH$_2$0, $R^8$=OCH$_3$, $R^C$=H)

Tetramethylguanidine (TMG) (0.255 g, 2.2 mmol) was added to a stirred solution of the product from 1e, L-phenylalanine methyl ester hydrochloride (0.16 g, 0.74 mmol), and chloroform (4 ml) chilled in an ice bath under N$_2$. The ice bath was removed and the reaction was allowed to come to room temperature and then stirred for 48 hours. CHCl$_3$ (25 ml) was added to the reaction mixture and the resulting solution was washed with 5% NaHCO$_3$ and brine, dried (MgSO$_4$), filtered and the filtrate was concentrated under vacuum to afford a crude product (0.69 g). The product was purified by flash chromatography (using CHCl$_3$, then CHCl$_3$:EtOAc (98:2)), to give the product (0.15 g, 42%) as a viscous gum; TLC, R$_f$=0.46, CHCl$_3$: EtOAc (8:2).

g. (Formula Ia, R$^1$=CH(CH$_3$)$_2$, R$^3$A=0CH$_2$OCO-, R$^B$=Formula IIb, R$^6$=CH$_2$O, R$^8$=OCH$_3$, R$^C$=H)

To a soluton of the product of Example 1f (0.15 g, 0.304 mmol) and dry CH$_2$Cl$_2$ (5.0 ml) was added Dess-Martin periodinane (1.29 g, 3.04 mmol). Trifluoroacetic acid (0.4 ml) was added and the solution was allowed to stir at room temperature under N$_2$ overnight. EtOAc (10 ml) was added and the mixture was extracted with saturated Na$_2$S$_2$O$_3$, saturated NaHCO$_3$ and brine. The organic layer was dried (MgSO$_4$) and concentrated under vacuum to afford, after purification by flash chromatography, (using CHCl$_3$, then MeOH:CHCl$_3$ (2:98)), the product (0.04 g) as an oil; TLc, R$_f$=0.9, MeOH:CHCl$_3$ (2:98). Analysis calculated for C$_{25}$H$_{28}$F$_2$N$_2$O$_6$.0.5 H$_2$O: C, 60.15; H, 5.85; N, 5.61
Found: C, 60.42; H, 5.69; N, 5.29

EXAMPLE 2

2-[[[4-[(1-Aminocarbonyl-2-phenylethyl)amino]-3,3-difluoro-1-(1-methylethyl)-2,4-dioxobutyl]amino]carbonyl]-1-pyrrolidinecarboxylic acid phenylmethyl ester (Formula Ib, R$^1$=CH(CH$_3$)$_2$, R$^3$A=0CH$_2$OCO-, R$^B$=Formula IIb, R$^6$=CH$_2$O, R$^8$=NH$_2$, R$^C$=H)

a. (Formula XVb, R$^1$=CH(CH$_3$)$_2$, R$^3$A=0CH$_2$OCO-)

WSCDI (24.04 g, 125.4 mmol) was added to a stirred solution of CBZ-L-proline ((28.4 g, 114.1 mmol), HOBT (30.00 g, 228.2 mmol), the product of Example 1d (20 g, 114.1 mmol) and dry THF (400 ml) at 0° C. under N$_2$. The resulting mixture was stirred at 0° C. for 1 hr; the cooling bath was removed and the mixture was allowed to warm to room temperature and was stirred at room temperature overnight. The THF was removed under vacuum to afford the crude product. The crude product was dissolved in ethyl acetate and the ethyl acetate solution was successively washed with 1N HCl, saturated NaHCO$_3$, and brine. The ethyl acetate solution was then dried (MgSO$_4$), filtered and the filtrate was concentrated under vacuum to afford, after purification by flash chromatography (CHCl$_3$:MeOH (98:2)), the product (35.03 g, 77%) as a yellow oil; TLC, R$_f$=0.7, CHCl$_3$:MeOH (95:5).

b. (Formula VIb, R$^1$=CH(CH$_3$)$_2$, R$^3$A=0CH$_2$OCO-)

A solution of the product from Example 2a (24.0 g, 60 mmol), p-toluenesulfonic acid (2.4 g, 12.6 mmol) and acetone (1600 ml) was stirred at room temperature for 5 hr. The acetone was removed under vacuum to leave an oily residue. This residue was dissolved in chloroform and the solution was washed with saturated NaHCO$_3$ and brine, dried (MgSO$_4$), filtered and the filtrate was concentrated under vacuum to give the product (17.67 g, 91%) as a light amber oil; TLC, R$_f$=0.46, CHCl$_3$:CH$_3$OH (95:5).

c. (Formula VIIb, R$^1$=CH(CH$_3$)$_2$, R$^3$A=0C-H$_2$OCO—)

A mixture of the product from Example 2b (2.50 g, 7.75 mmol), ethyl 2-bromo-2,2-difluoroacetate (1.57 g, 7.75 mmol), activated zinc (0.505 g, 7.75 mmol) and dry THF (125 ml) was heated at gentle reflux under nitrogen for 1 hr. The mixture was then allowed to cool to just below reflux and additional ethyl 2-bromo-2,2-difluoroacetate (1.57 g, 7.75 mmol) and activated zinc (0.505 g, 7.75 mmol) were added. The reaction mixture was again heated to gentle reflux and kept at reflux for 3 hr. The mixture was cooled and ethyl acetate (400 ml) was added. The ethyl acetate solution was washed with 1N KHSO$_4$ solution and brine, dried over MgSO$_4$, filtered and the filtrate was concentrated under vacuum to afford a crude product (3.7 g). The product was purified by flash chromatography (EtOAc:hexane (1:1) to give 1.53 g (45% yield) of the desired product as a light yellow waxy solid; TLC, R$_f$=0.45, petroleum ether-:EtOAc (33:66).

d. (Formula IXb, R$^1$=CH(CH$_3$)$_2$, R$^3$A=0CH$_2$OCO—)

1N Sodium hydroxide solution (2.75 ml, 2.75 mmol) was added to a stirred solution of the product from Example 2c (1.0 g, 2.19 mmol) and methanol (15 ml) at room temperature. The resulting solution was stirred at room temperature for 4 hr. The reaction mixture was treated with water (75 ml) and the resulting solution was extracted with EtOAc. The aqueous layer was made acidic (pH 2) with 1NHCl. The acidic aqueous mixture was extracted with ethyl acetate, and the ethyl acetate layer was washed with brine, dried (MgSO$_4$), filtered and the filtrate was concentrated under vacuum to give the product (0.883 g, 94.1% yield) as a white foam; TLC, R$_f$=0.1, CHCl$_3$: MeOH:HOAc (95:5:0.5).

e. (Formula VIIIb, R$^1$=CH(CH$_3$)$_2$, R$^3$A=0C-H$_2$OCO—, R$^B$=Formula IIb, R$^6$=CH$_2$O, R$^8$=NH$_2$, R$^C$=H)

WSCDI was added to a stirred solution of the product from Example 2d (0.25 g, 0.583 mmol), L-phenylalanine amide (0.10 g, 0.609 mmol), HOBT (0.087 g, 0.64 mmol), and dry THF (10 ml) at 0° C. under N$_2$. The resulting mixture was stirred at 0° C. for 1 hr; then the cooling source was removed and the reaction mixture was allowed to warm to room temperature and stir at room temperature overnight. The mixture was concentrated under vacuum, and the resulting residue was dissolved in ethyl acetate. The ethyl acetate solution was washed, successively, with 1N HCl, saturated NaHCO$_3$ and brine, dried (MgSO$_4$), filtered and the filtrate was concentrated under vacuum to afford, after purification by flash chromatography (CHCl$_3$:MeOH (95:5)), the product (72%); TLC, R$_f$=0.58, CHCl$_3$:CH$_3$OH (90:10).

f. (Formula Ib, R$^1$=CH(CH$_3$)$_2$, R$^3$A=0CH$_2$OCO—, R$^B$=Formula IIb, R$^6$=CH$_2$O, R$^8$=NH2, R$^C$=H)

Acetic anhydride (3 ml, 27.2 mmol) was added to a stirred solution of the product from Example 2e (0.23 g, 0.4 mmol) and dry DMSO (3 ml, 34.8 mmol) at room temperature under N$_2$. The resulting mixture was stirred overnight at room temperature. The mixture was then poured onto ice/water (40 ml) and stirred vigorously for 3 hr. The aqueous mixture was extracted (2 times) with ethyl acetate. The ethyl acetate layer was washed (2 times) with saturated NaHCO$_3$ and brine, dried (MgSO$_4$), filtered and the filtrate concentrated under water vacuum to afford, after purification by flash chromatography (CHCl$_3$:MeOH (95:5)) the product (0.18 g, 79%); TLC, R$_f$=0.68, CHCl$_3$:CH$_3$OH (90:10).

Analysis calculated for C$_{29}$H$_{34}$F$_2$N$_4$O$_6$.1.0 H$_2$O: C, 58.97; H, 9.14; N, 9.49 Found: C, 59.07; H, 6.03; N, 9.15

EXAMPLE 3

N-[2,2-Difluoro-5-methyl-1,3-dioxo-4-[[[1-[(phenylmethoxy)carbonyl]-2-pyrrolidinyl]carbonyl]amino]-hexyl]-L-seryl-L-phenylalaninamide (Formula Ib, $R^1=CH(CH_3)_2$, $R^3A=OCH_2OCO-$, $R^B=$Formula IIa, $R^6=CH_2OH$, Rhu $7=CH_2O$, $R^8=NH_2$, $R^C=H$)

a. (Formula XXVIb, $R^1=CH(CH_3)_2$, $R^3A=OCH_2OCO-$)

A solution of the product of Example 2c (1.3 g, 2.85 mmol) and $CH_3Cl_2$ (5.0 ml) was added to a stirred mixture of Dess-Martin periodinane (4.83 g, b 11.39 mmol) and $CH_2Cl_2$ (35 ml). Trifluoroacetic acid (0.89 ml) was added and the reaction mixture was stirred at room temperature under $N_2$ overnight. Ethyl acetate (200 ml) was added and the mixture was extracted with saturated $Na_2S_2O_3$, saturated $NaHCO_3$ and brine. The organic layer was dried ($MgSO_4$), filtered and concentrated under vacuum to afford, after purification by flash chromatography ($MeOH:CHCl_3$ (1:99)), the product (0.53 g); TLC, $R_f=0.65$, MeOH: $CHCl_3$ (2:98).

b. (Formula XXVIIb, $R^1=CH(CH_3)_2$, $R^3A=OCH_2OCO-$)

To a solution of the product of Example 3a (2.0 g, 4.4 mmol) and MeOH (20 ml) and was added 1N NaOH (6.16 ml, 6.16 mmol). The solution was stirred at room temperature for 3 hr. The MeOH was removed under vacuum and $H_2O$ (75 ml) was added to the residue. The aqueous solution was extracted with EtOAc and the EtOAc layer was discarded. The aqueous solution was taken to pH 2.0 with 1N HCl and extracted 3 times with EtOAc. The combined organic layers were washed with brine, dried ($MgSO_4$), filtered and concentrated under vacuum to give the product (1.51 g, 80.5%) as a white foam; NMR (DMSO-$d_6$): 0.82 (m,6), 1.8 (m,3), 2.17 (m,2), 3.4 (m,2), 4.36 (m,1), 4.7 (m,1), 4.95 (m,2), 7.3 (m,5), 8.37 (m,1).

c. (Formula Ib, Rhu $1=CH(CH_3)_2$, $R^3A=OCH_2OCO-$, $R^B=$Formula IIa, $R^6=CH_2OH$, $R^7=CH_2O$, $R^8=NH_2$, $R^C=H$)

Using the method of Example 2e, the product from Example 3b was allowed to react with L-serine-L-phenylalanineamide and one equivalent of N-methylmorpholine to afford, after purification by flash chromatography ($MeOH:CHCl_3$ (5:95)), the product (44%); TLC, $L_f=0.50$, $MeOH:CHCl_3$ (10:90).

Analysis calculated for $C_{32}H_{39}F_2N_5O_8 \cdot 0.75H_2O$: C, 57.09; H, 6.06; N, 10.40 Found: C, 57.14; H, 5.96; N, 10.07

EXAMPLE 4

2-[[[3,3-Difluoro-4-[(1-methoxycarbonyl-2-phenylethyl)amino]-1-(1-methylethyl)-2,4-dioxobutyl]amino]carbonyl]-1-pyrrolidinecarboxylic acid phenylmethyl ester (Formula Ib, $R^1=CH(CH_3)_2$, $R^3A=OCH_2OCO-$, $R^B=$Formula IIb, $R^6=H$, $R^8=OCH_3$, $R^C=H$)

Using the method of Example 2e, product prepared using the method of Example 3b was allowed to react with L-phenylalanine methyl ester hydrochloride and one equivalent of N-methylmorpholine. The reaction afforded, after purification by flash chromatography ($MeOH:CHCl_3$ (5:95)), the title product (62%); TLC, $R_f=0.65$, $MeOH:CHCl_3$ (5:95).

Analysis calculated for $C_{30}H_{35}F_2N_3O_7$: C, 61.32; H, 6.00; N, 7.15 Found: C, 61.25; H, 6.08; N, 7.15

EXAMPLE 5

2-[[[4-[(1-Carboxy-2-phenylethyl)amino]-3,3-difluoro-1-(methylethyl)-2,4-dioxobutyl]amino]carbonyl]-1-pyrrolidinecarboxylic acid phenylmethyl ester (Formula Ib, $R^1=CH(CH_3)_2$, $R^3A=OCH_2OCO-$, $R^B=$Formula IIb, $R^6=CH_2O$, $R^8=OH$, $R^C=H$)

Using the method of Example 3b, product prepared according to the method of Example 4 was allowed to react with 1N NaOH to afford the product (67%); HPLC, $t_R=7.92$ min, $CH_3CN:H_2O$ (45:55), 2.0 ml/min, $C_{18}$ column.

Analysis calculated for $C_{29}H_{33}F_2N_3O_7 \cdot H_2O$: C, 58.87; H, 5.96; N, 7.10 Found: C, 58.63; H, 5.68; N, 6.90

EXAMPLE 6

(No example for this number.)

EXAMPLE 7

2-[[[3,3-difluoro-4-[(methoxycarbonylmethyl)amino]-1-(1-methylethyl-2,4-dioxobutyl]amino]carbonyl]-1-pyrrolidinecarboxylic acid phenylmethyl ester (Formula Ib, $R^3A=OCH_2OCO-$, $R^1=CH(CH_3)_2$, $R^B=$formula IIb, $R^6=H$, $R^8=-OCH_3$, $R^C=H$)

a. (Formula VIIIa, $R^3A=OCH_2OCO-$, $R^1=CH(CH_3)_2$, $R^B=$formula IIb, $R^6=H$, $R^8=OCH_3$, $R^C=H$)

Using the method of Example 2e, a product prepared by the method of Example 2d was allowed to react with glycine methyl ester hydrochloride and 1 equivalent of N-methylmorpholine to afford a product (86%); TLC, $R_f 0.38$, $MeOH:CHCl_3$ (5:95), silica gel.

b. (Formula Ib, $R^3A=OOCO-$, $R^1=CH(CH_3)_2$, $R^B=$formula IIb, $R^6=H$, $R^8=OCH_3$, $R^C=H$)

To a solution of the product of Example 7a (0.97 g, 1.94 mmoles) and dry $CH_2Cl_2$ (25 ml) was added Dess-Martin periodinane (4.13 g, 9.71 mmoles). Trifluoroacetic acid (0.76 ml) was added and the solution was allowed to stir at room temperature under $N_2$ overnight. EtOAc (50 ml) was added and the mixture was poured into saturated $NaHCO_3$ containing $Na_2S_2O_3$ (8 g, 32 mmoles) and stirred vigorouslyfor 2 minutes. The EtOAc layer was separated and extracted with saturated $NaHCO_3$ and brine. The EtOAc solution was concentrated under vacuum to afford, after purification by flash chromatography ($MeOH:CHCl_3$, 2:98), a product (55%); TLC, $R_f=0.65$, silica, $CHCl_3:MeOH$ (95:5).

Analysis calculated for: $C_{23}H_{29}F_3N_3O_7 \cdot 0.25\ H_2O$: C, 55.03; H, 5.92; N, 8.37 Found: C, 55.09; H, 5.84; N, 8.21

EXAMPLE 8 b  2-[[[4-[(carboxymethyl)amino]-3,3-difluoro-1-(1-methylethyl)-2,4-dioxobutyl]amino]carbonyl]-1-pyrrolidinecarboxylic acid phenylmethyl ester (Formula Ib, $R^3A=OCH_2OCO-$, $R^1=CH(CH_3)_2$, $R^B=$formula IIb, $R^6=H$, $R^8=OH$, $R^C=H$)

Using the method of Example 3b, but using $H_2O$:-MeOH in a ratio of 1:4 and allowing the reaction to stir overnight, the product of Example 7b was allowed to react with 1N NaOH to afford, after purifying by flash chromatography on acidic silica gel ($MeOH:CHCl_3$, (5:95)), a product (44%); TLC, $R_f=-0.25$ and 0.32 ($CH_3OH: CHCl_3:HOAc$, 5:95:0.1).

Analysis calculated for $C_{22}H_{27}F_2N_3O_7 \cdot 0.5\ H_2O$: C, 53.66; H, 5.73; N, 8.53 Found: C, 53.55; H, 5.53; N, 8.15

EXAMPLE 9

N-[N-[2,2-difluoro-5methyl-1,3-dioxo-4-[[[1-[(phenylmethoxy)carbonyl]-2-pyrrolidinyl]carbonyl]amino]hexyl]-L-phenylalanyl]glycine methyl ester (Formula Ib, $R^3A=0CH_2OCO-$, $R^1=CH(CH_3)_2$, $R^B=$formula IIa, $R^6=CH_2O-$, $R^7=H$, $R^8=OCH_3$, $R^C=H$)

a. (N-Benzyloxycarbonyl-L-phenylalanylglycine methyl ester)

Using the method of Example 7a, CBZ-L-phenylalanine was allowed to react with glycine methyl ester hydrochloride to afford, after purification by flash chromatography ($CHCl_3$), a product (61%); TLC, $R_f=0.69$, MeOH:$CHCl_3$ (5:95), silica gel.

b. (L-Phenylalanylglycine methyl ester)

The compound of Example 9a (2.2 g, 5.94 mmoles) was placed in absolute EtOH (250 ml) and warmed to effect solution. After cooling to room temperature, 10% Pd/C was added and the mixture was hydrogenated on a Parr shaker at 3 atmospheres of $H_2$ for 3 hours. The mixture was filtered through diatomaceous earth (Celite). The filtrate was concentrated under reduced pressure to give a product (1.32 g, 94%) as a pale yellow oil. The product was used without further purification.

c. (Formula VIIIb, $R^3A=0CH_2OCO-$, $R^1=CH(CH_3)_2$, $R^B=$formula IIa, $R^6=CH_2O$, $R^7=H$, $R^8=OCH_3$, $R^C=H$)

Using the method of Example 2e, a product prepared by the method of Example 2d was allowed to react with the product of Example 9b to afford, without further purification, a product (84%); TLC; $R_f=0.55$, MeOH:$CHCl_3$ (5:95), silica gel.

d. (Formula Ib, $R^3A=0CH_2OCO-$, $R^1=CH(CH_3)_2$, $R^B=$formula IIa, $R^6=CH_2O-$, $R^7=H$, $R^8=OCH_3$, $R^C=H$)

Using the method of Example 7b, the product of Example 9c was oxidized to afford, after purification by flash chromatography ($CHCl_3$, $CH_3OH$:$CHCl_3$ (3:97)), the product title (48%); TLC, $R_f=0.62$, MeOH:$CHCl_3$ (5:95), silica.

Analysis calculated for $C_{32}H_{38}F_2N_4O_8.0.5H_2O$: C, 58.79; H, 6.01; N, 8.37 Found: C, 58.65; H, 5.89; N, 8.41

EXAMPLE 10

N-[N-[2,2-difluoro-5-methyl-1,3-dioxo-4[[[1-[(phenylmethoxy)carbonyl]-2-pyrrolidinyl]carbonyl]amino]hexyl]-L-phenylalanyl]glycine (Formula Ib, $R^3A=0CH_2OCO-$, $R^1=CH(CH_3)_2$, $R^B=$formula IIa, $R^6=CH_2O$, $R^7=H$, $R^8=OH$, $R^C=H$)

Using the method of Example 8a, the product of Example 9d was allowed to react with 1N NaOH for 2 hours to afford, after purification by flash chromatography on acidic silica gel ($CHCl_3$, MeOH:$CHCl_3$ (3:97)), the title product (61%); TLC, $R_f=0.48$, silica gel, $CHCl_3$:MeOH:HOAc (95:5:0.1).

Analysis calculated for $C_{31}H_{36}F_2N_4O_8 \cdot H_2O$: C, 57.40; H, 5.90; N, 8.63 Found: C, 57.29; H, 5.74; N, 8.36

EXAMPLE 11

$N^2$-[2,2-difluoro-5-methyl-1,3-dioxo-4-[[[1-[(phenylmethoxy)carbonyl]-2-pyrrolidinyl]carbonylamino]hexyl]-$N^6$-[phenylmethoxy)carbonyl]-L-lysine phenylmethyl ester (Formula Ib, $R^3A=0CH_2OCO-$, $R^1=CH(CH_3)_2$, $R^B=$formula IIb, $R^6=0CH_2OCONH(CH_2)_4-$, $R^8=OCH_2O$, $R^C=H$)

a. (Formula VIIIb, $R^3A=0CH_2OCO-$, $R^1=CH(CH_3)_2$, $R^B=$formula IIb, $R^6=0CH_2OCONH(CH_2)_4-$, $R^8=OCH_2O$, $R^C=H$)

Using the method of Example 7a, a product prepared by the method of Example 2d was allowed to react with ε-CBZ-L-lysine benzyl ester hydrochloride to afford, without further purification, a product (88%); TLC, $R_f=0.68$, silica gel, MeOH:$CHCl_3$ (95:5).

b. (Formula Ib, $R^3A=0CH_2OCO-$, $R^1=CH(CH_3)_2$, $R^B=$formula IIb, $R^6=0CH_2OCONH(CH_2)_4-$, $R^8=OCH_2O$, $R^C=H$)

Using the method of Example 7b, the product of Example 11a was oxidized to afford, after purification by flash chromatography (MeOH:$CHCl_3$ (2:98)), the title product (62%); HPLC, $t_R=8.79$ min, 2 ml/min, $H_2O$:$CH_3CN$:THF:TFA (55:35:15:0.1), $C_8$ column.

Analysis calculated for $C_{41}H_{48}F_2N_4O_9.0.5\ H_2O$: C, 62.50; H, 6.14; N, 7.11 Found: C, 62.47; H, 6.15; N, 7.08

EXAMPLE 12

$N^2$-[2,2-difluoro-5-methyl-1,3-dioxo-4-[[[1-[(phenylmethoxy)carbonyl]-2-pyrrolidinyl]carbonyl]amino]hexyl]-$N^6$-[(phenylmethoxy)carbonyl]-L-lysine (Formula Ib, $R^3A=0CH_2OCO-$, $R^1=CH(CH_3)_2$, $R^B=$formula IIb, $R^6=0CH_2OCONH(CH_2)_4-$, $R^8=OH$, $R^C=H$)

Using the method of Example 8a, the product of Example 11b was allowed to react with 1N NaOH for 18 hours to afford, after purification by flash chromatography on acidic silica gel (MeOH:$CHCl_3$ (2:98)), the title product (55%); TLC, $R_f=0.41$, silica gel, MeOH:$CHCl_3$:HOAc (5:95:0.1).

Analysis calculated for $C_{34}H_{42}F_2N_4O_9 \cdot H_2O$: C, 57.78; H, 6.27; N, 7.92 Found: C, 57.97; H, 6.03; N, 7.85

EXAMPLE 13

N-[2,2-difluoro-5-methyl-1,3-dioxo-4-[[[1-[(phenylmethoxy)carbonyl]-2-pyrrolidinyl]carbonyl]amino]hexyl]-L-glutamic acid 1-methyl 5-(phenylmethyl) ester (Formula Ib, $R^3A=0CH_2OCO-$, $R^1=CH(CH_3)_2$, $R^B=$formula IIb, $R^6=0CH_2OCONH(CH_2)_2-$, $R^8=OCH_2O$, $R^C=H$)

a. (Formula VIIIb, $R^3A=0CH_2OCO-$, $R^1=CH(CH_3)_2$, $R^B=$formula IIb, $R^6=0CH_2OCONH(CH_2)_2-$, $R^8=OCH_2O$, $R^C=H$)

Using the method of Example 7a, a product prepared by the method of Example 2d was allowed to react with L-α,γ-dibenzylglutamate tosylate to afford, without further purification, a product (52%); TLC; $R_f=0.6$, silica gel, MeOH:$CHCl_3$ (5:95).

b. (Formula Ib, $R^3A=0CH_2OCO-$, $R^1=CH(CH_3)_2$, $R^B=$formula IIb, $R^6=0CH_2OCONH(CH_2)_2-$, $R^8=OCH_2O$, $R^C=H$)

Using the method of Example 7b, the product of example 13a was oxidized to afford, after purification by flash chromatogrpahy ($CHCl_3$), the title product (57%); TLC, $R_f=0.74$, silica gel, MeOH:—$CHCl_3$ (5:95).

Analysis calculated for $C_{39}H_{43}F_2N_3O_9.1.75\ H_2O$: C, 61.05; H, 6.10; N, 5.47 Found: C, 61.04; H, 5.67; N, 5.51

EXAMPLE 14

2-[[[3,3-difluoro-1-(1-methylethyl)-2,4-dioxo-4-[[2-phenyl-1-[(phenylmethoxy)carbonyl]ethyl]amino]butyl]amino]-carbonyl]-1-pyrrolidinecaboxylic acid phenylmethyl ester (Formula Ib, $R^3A=0CH_2OCO-$, $R^1=CH(CH_3)_2$, $R_B=$formula IIb, $R^6=CH_2O$, $R^8=OCH_2O$, $R^C=H$)

a. (Formula VIIIb, $R^3A=0CH_2OCO-$, $R^1=CH(CH_3)_2$, $R^B=$formula IIb, $R^6CH_2O$, $R^8=OCH_2O$, $R^C=H$)

Using the method of Example 7a, a product prepared by the method of Example 2d was allowed to react with L-phenylalanine benzyl ester tosylate to afford, without further purification, a product (84%); TLC, $R_f=0.52$ and 0.65, silica gel, MeOH:CHCl$_3$ (5:95).

b. (Formula Ib, $R^3A=OCH_2OCO-$, $R^1=CH(CH_3)_2$, $R^B=$formula IIb, $R^6=CH_2O$, $R^8=OCH_2O$, $R^C=H$)

Using the method of Example 7b the product of Example 14a was oxidized to afford, after purification by flash chromatography (CHCl$_3$) the title product (29%); TLC, $R_f=0.81$, silica gel, MeOH:CHCl$_3$ (5:95).

Analysis calculated for $C_{36}N_{40}F_2N_3O_7.0.5\ H_2O$: C, 64.18; H, 6.13; N, 6.24 Found: C, 64.23; H, 5.88; N, 6.14

EXAMPLE 15

2-[[[3,3-difluoro-1-(1-methylethyl)-2,4-dioxo-4-[[[(phenyl-methoxy)carbonylmethyl]amino]butyl]amino]carbonyl]-1-pyrrolidinecarboxylic acid phenylmethyl ester (Formula Ib, $R^3A=OCH_2OCO-$, $R^1=CH(CH_3)_2$, $R^B=$formula IIb, $R^6=H$, $R^8=OCH_2O$, $R^C=H$)

a. (Formula VIIIb, $R^3A=OCH_2OCO-$, $R^1=CH(CH_3)_2$, $R^B=$formula IIb, $R^6=H$, $R^8=OCH_2O$, $R^C=H$)

Using the method of Example 7a a product prepared by the method of Example 2d was allowed to react with glycine benzyl ester tosylate to afford, without further purification, a product (84%); TLC, $R_f=0.58$, silica gel, MeOH:CHCl$_3$ (5:95).

b. (Formula Ib, $R^3A=OCH_2OCO-$, $R^1=CH(CH_3)_2$, $R^B=$formula IIb, $R^6=H$, $R^8=OCH_2O$, $R^C=H$)

Using the method of Example 1g, but using 5 equivalents of Dess-Martin Periodinane reagent, the product of Example 15a was oxidized to afford, after purification by flash chromatography (CHCl$_3$) the title product (76%); TLC, $R_f=0.67$, silica gel, MeOH:CHCl$_3$ (3:97).

Analysis calculated for $C_{29}H_{33}F_2N_3O_7.0.5\ H_2O$: C, 59.78; H, 5.88; N, 7.21 Found: C, 59.73; H, 5.64; N, 7.19;

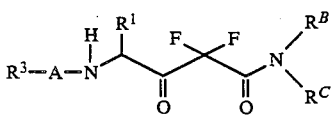 Ia

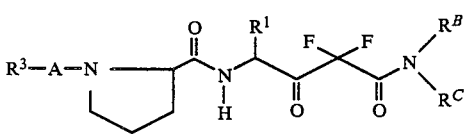 Ib

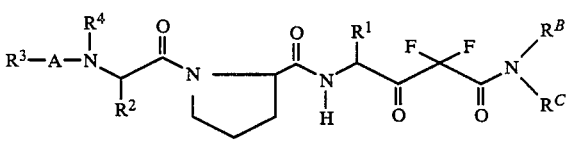 Ic

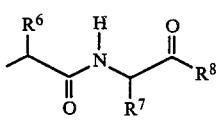 IIa

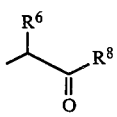 IIb

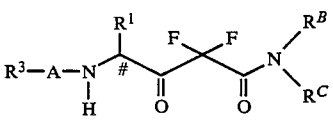 IIIa

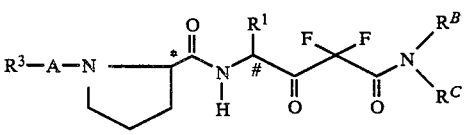 IIIb

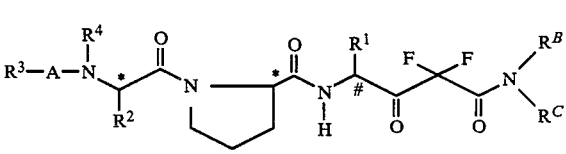 IIIc

-continued
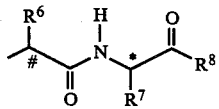 IIId
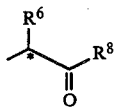 IIIe
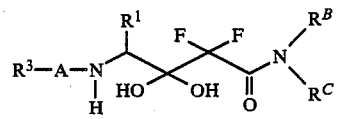 IVa
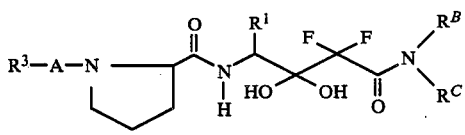 IVb
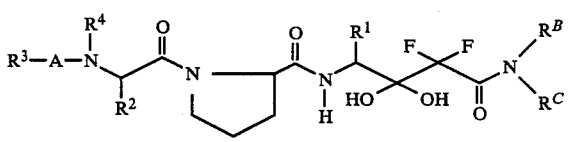 IVc
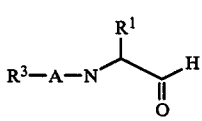 VIa
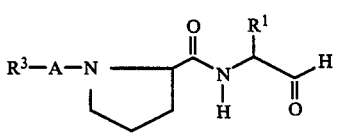 VIb
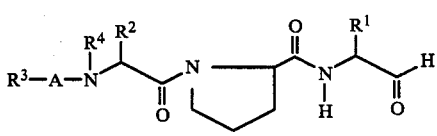 VIc
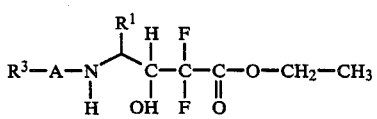 VIIa
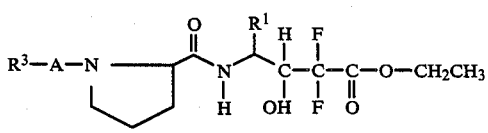 VIIb
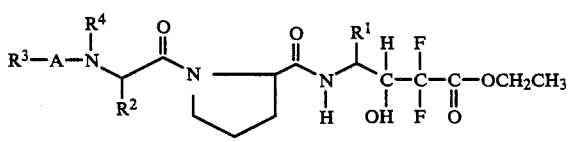 VIIc
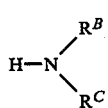 V -continued
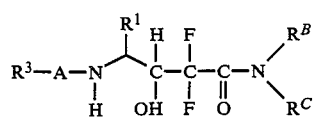 VIIIa
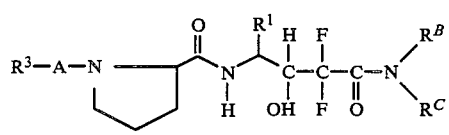 VIIIb
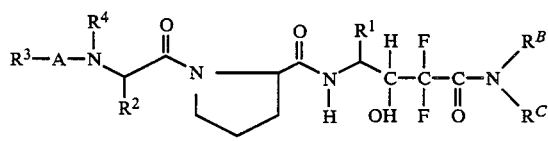 VIIIc
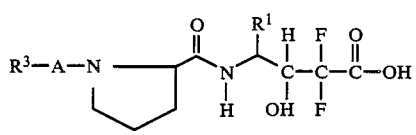 IXb
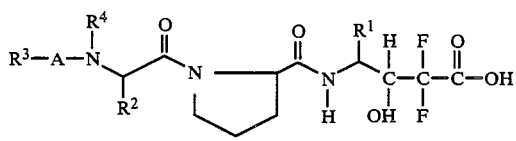 IXc
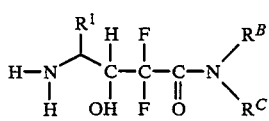 XIa
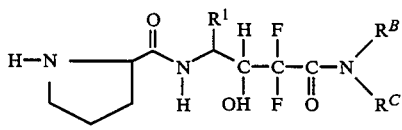 XIb
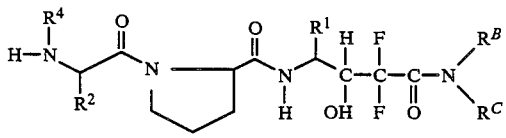 XIc
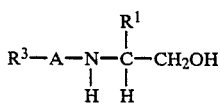 XIVa
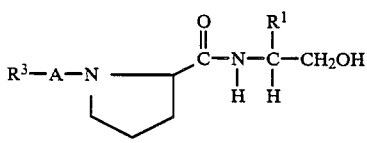 XIVb
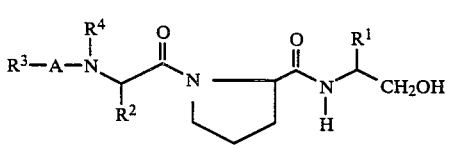 XIVc
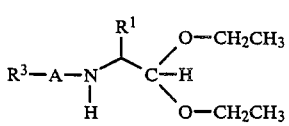 XVa -continued
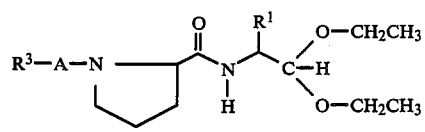 XVb
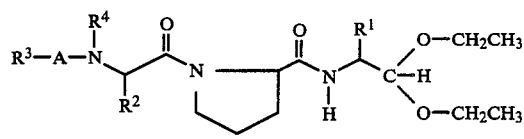 XVc
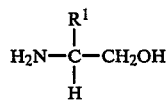 XVI
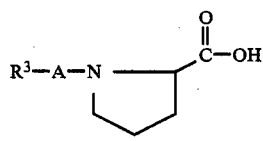 XVIIb
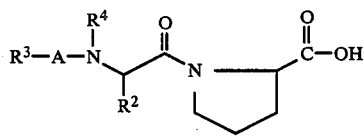 XVIIc
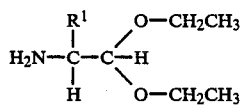 XVIIIa
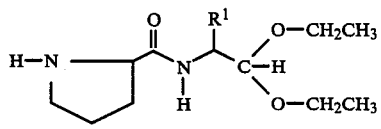 XVIIIb
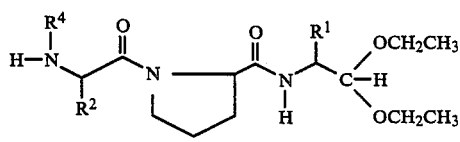 XVIIIc
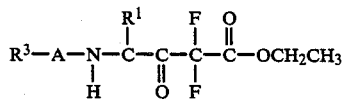 XXVIa
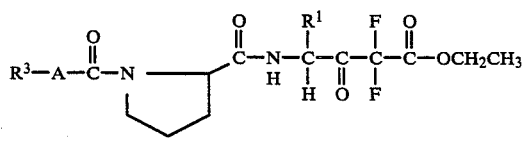 XXVIb
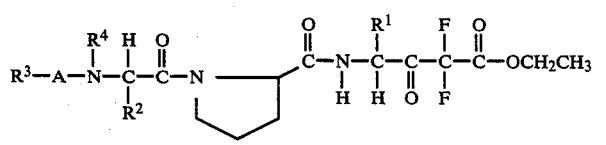 XXVIc
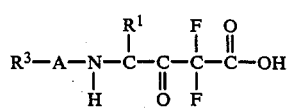 XXVIIa

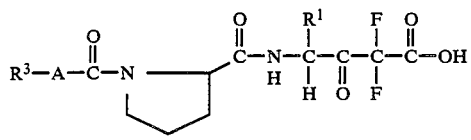

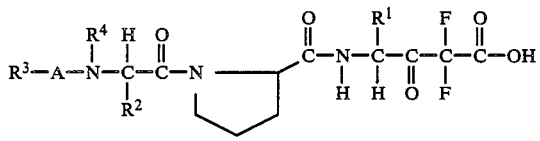

XXVIIb

XXVIIc

What is claimed is:
1. A compound of formula Ib

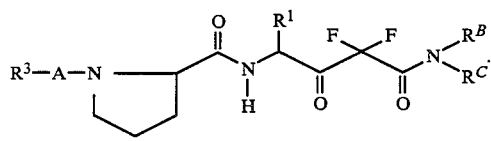

wherein
$R^1$ is an alkyl group containing 3 carbons;
$R^3$ is benzyl;
A is —OCO—;
$R^C$ is hydrogen; and
$R^B$ is selected from a group consisting of (a) formula IIa

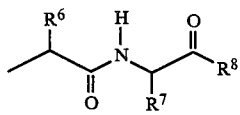

wherein
$R^6$ is hydroxymethyl or phenylmethyl and $R^7$ is hydrogen or phenylmethyl, and (b) formula IIb $$\underset{O}{\overset{R^6}{\underset{|}{\text{—}}}}\text{—}R^8 \quad \text{IIb}$$

wherein
$R^6$ is hydrogen, phenylmethyl, 4-[(phenylmethoxy)carbonyl]butyl or 2-[(phenylmethoxy)carbonyl]ethyl; and
$R^8$ is methoxy, hydroxy or phenylmethoxy, or a pharmaceutically acceptable salt thereof.

2. A pharmaceutical composition comprising a compound of claim 1 in an amount sufficient to inhibit human leukocyte elastase in a living mammal in association with a pharmaceutically acceptable diluent or carrier.

3. A composition as claimed in claim 2 wherein said composition is in the form of a liquid or powdered aerosol.

4. A method of treating emphysema in a living mammal comprising administering to the mammal a pharmacologically effective amount of a compound of claim 1.

* * * * *